United States Patent [19]
Kuroshaki et al.

[11] Patent Number: 5,660,182
[45] Date of Patent: Aug. 26, 1997

[54] INFLATABLE CUFF USED FOR BLOOD PRESSURE MEASUREMENT AND AUTOMATIC BLOOD PRESSURE MEASURING APPARATUS INCLUDING INFLATABLE CUFF

[75] Inventors: Takeshi Kuroshaki, Kasugai; Satoshi Koike, Aichi-ken; Hideto Tsuchida, Gifu; Chikao Harada; Takashi Nomura, both of Komaki, all of Japan

[73] Assignee: Colin Corporation, Aichi-ken, Japan

[21] Appl. No.: 306,987

[22] Filed: Sep. 16, 1994

[30] Foreign Application Priority Data

| Sep. 20, 1993 | [JP] | Japan | 5-050979 U |
| Oct. 15, 1993 | [JP] | Japan | 5-055901 U |
| Oct. 15, 1993 | [JP] | Japan | 5-055902 U |
| Oct. 15, 1993 | [JP] | Japan | 5-055903 U |
| Nov. 17, 1993 | [JP] | Japan | 5-061928 U |

[51] Int. Cl.$^6$ .................................................. A61B 5/00
[52] U.S. Cl. .................................. 128/686; 606/202
[58] Field of Search ........................... 128/686, 671–683; 606/201, 202

[56] References Cited

U.S. PATENT DOCUMENTS

| 3,279,459 | 10/1966 | Schenker | 128/686 |
| 3,669,096 | 6/1972 | Hurwitz | 128/686 |
| 3,699,945 | 10/1972 | Hanafin | 128/686 |
| 3,812,844 | 5/1974 | Sokol | 128/686 |
| 4,605,010 | 8/1986 | McEwen | 128/686 |
| 4,770,175 | 9/1988 | McEwen | 128/686 |
| 4,920,971 | 5/1990 | Blessinger | |
| 5,179,957 | 1/1993 | Williams | 128/686 |
| 5,201,758 | 4/1993 | Glover | 128/686 |
| 5,433,724 | 7/1995 | Kawasaki et al. | 606/202 |

FOREIGN PATENT DOCUMENTS

| A-62-170002 | 10/1987 | Japan . |
| A-63-145636 | 6/1988 | Japan . |

*Primary Examiner*—Robert Nasser
*Attorney, Agent, or Firm*—Oliff & Berridge

[57] ABSTRACT

An inflatable cuff for pressing a body portion of a living subject by being wound and inflated around the body portion, in measuring a blood pressure of the subject, the cuff having (a) a first group of graduations provided on a major surface of the cuff, the major surface being adapted to be visible when the cuff is wound around the body portion of the subject, so that the first group of graduations are used for measuring a circumferential length of the body portion; and (b) a second group of graduations provided on the major surface of the cuff, the graduations of the second group corresponding to the graduations of the first group, respectively, so that the cuff wound around the body portion of the subject is fixed at one of the graduations of the second group which corresponds to one of the graduations of the first group which indicates the measured circumferential length of the body portion.

28 Claims, 16 Drawing Sheets

FIG. 7
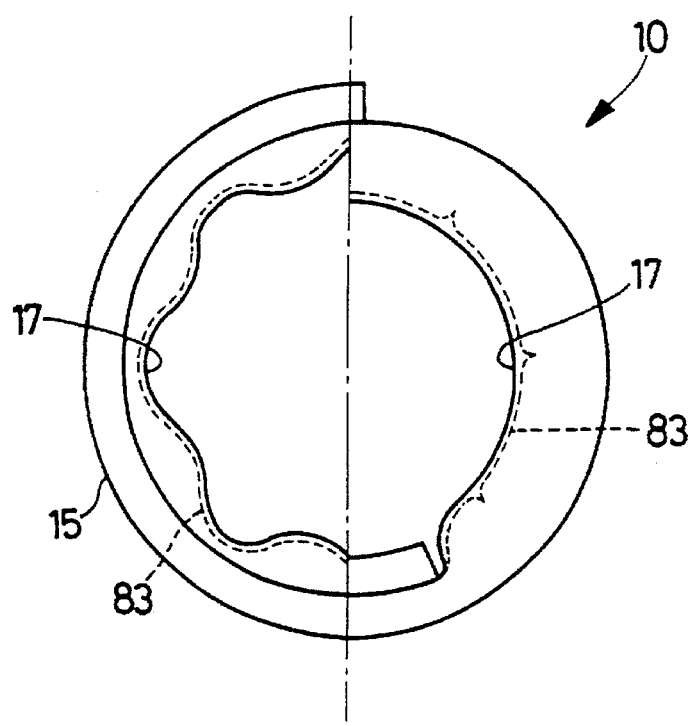
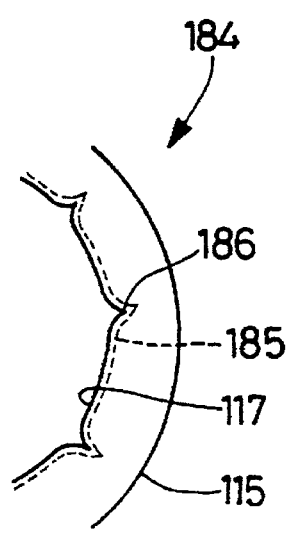
FIG. 9
PRIOR ART

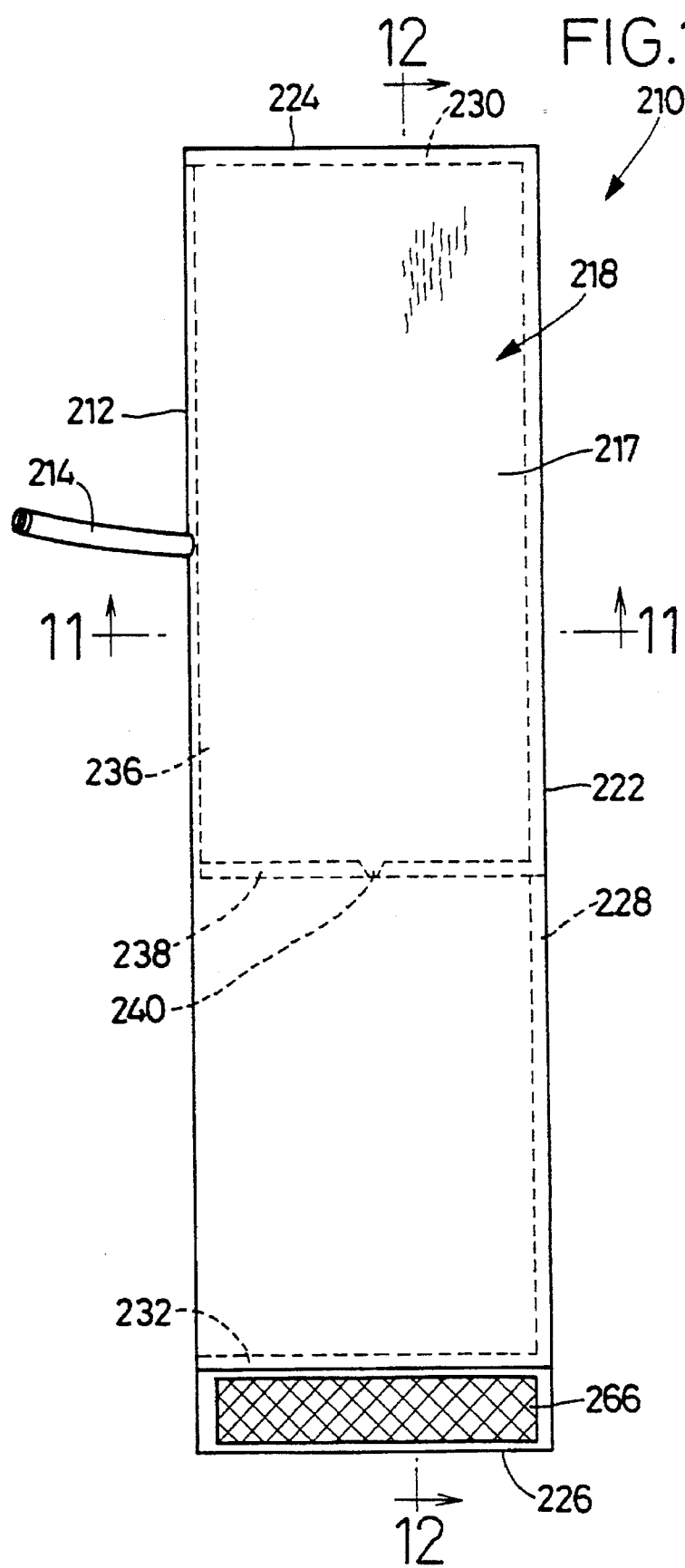

INFLATABLE CUFF USED FOR BLOOD PRESSURE MEASUREMENT AND AUTOMATIC BLOOD PRESSURE MEASURING APPARATUS INCLUDING INFLATABLE CUFF

BACKGROUND OF THE INVENTION

1. Field of the Invention

The present invention relates to an inflatable cuff which is adapted to be wound around a body portion of a living subject in measuring a blood pressure of the subject, and also relates to an automatic blood pressure measuring apparatus including an inflatable cuff.

2. Related Art Statement

There is known an inflatable cuff for use in measuring a blood pressure of a living subject. The cuff has an inflatable chamber which inflates upon supplying thereto of a pressurized air. The cuff is used by being wound around a body portion of the subject so that it is inflated to occlude arteries of the body portion. For obtaining an accurate blood pressure of the subject, it is required that the cuff be wound around the body portion with an appropriate and uniform pressing force over the entire circumferential length of the body portion (e.g., upper arm).

However, the subject's body portion around which the cuff is wound does not have a precisely cylindrical shape and, in fact, it has the shape of a truncated cone. For example, regarding an upper arm that is commonly used as the body portion around which the cuff is wound, it is empirically known that a circumferential length of the arm measured at a proximal edge (i.e., edge nearer to the shoulder) of the cuff wound around the arm is greater than another measured at a distal edge (i.e., edge nearer to the elbow) of the cuff. In addition, a thicker arm has a greater difference between the above-identified two circumferential lengths. For winding a cuff around a thick arm with an appropriate, uniform pressing force over the entire circumferential length of the arm, it is required that the cuff be so wound as to comply with the profile of the arm. An appropriate winding of a cuff around a precisely cylindrical body portion could be effected in such a way that one of the opposite edges of the cuff cylindrically wound around the body portion is positioned in one plane perpendicular to the center line of the cylindrical cuff. However, in the case where a cuff is wound around a body portion having a truncated-conical shape, an appropriate winding of the cuff needs the skill of a user such as a doctor or a nurse because the cuff has no means to which the user can refer. Thus, in this case, an accurate blood pressure measurement may not be obtained.

SUMMARY OF THE INVENTION

It is therefore an object of the present invention to provide an inflatable cuff which can easily be wound around a body portion of a living subject with an appropriate, substantially uniform pressing force over the entire circumferential length of the body portion.

According to the first aspect of the present invention, there is provided an inflatable cuff for pressing a body portion of a living subject by being wound and inflated around the body portion, in measuring a blood pressure of the subject, wherein the improvement comprises (a) a first group of graduations provided on a major surface of the cuff, the major surface being adapted to be visible when the cuff is wound around the body portion of the subject, so that the first group of graduations are used for measuring a circumferential length of the body portion; and (b) a second group of graduations provided on the major surface of the cuff, the graduations of the second group corresponding to the graduations of the first group, respectively, so that the cuff wound around the body portion of the subject is fixed at one of the graduations of the second group which corresponds to one of the graduations of the first group which indicates the measured circumferential length of the body portion.

The inflatable cuff in accordance with the first aspect of the invention can easily be wound around the body portion of the subject with an appropriate, uniform pressing force over the entire circumferential length of the body portion, by referring to one of the graduations of the second group which corresponds to one of the graduations of the first group which indicates the measured circumferential length of the body portion. That is, the present cuff can be fixed at a circumferential length thereof corresponding to the above-mentioned one graduation of the second group. Thus, the present cuff can appropriately be used without needing the skill of a user, and a reliable blood pressure measurement can easily be effected using the cuff. The second group of graduations are provided on the cuff based on the empirical knowledge that the difference between the respective circumferential lengths of the body portion measured at the opposite edges of the cuff wound therearound changes with one or both of the two circumferential lengths. For example, regarding an upper arm as the body portion, the empirical knowledge teaches that a thicker arm has a greater difference between the two circumferential lengths of the arm measured at the proximal and distal edges of the cuff wound therearound (the proximal circumferential length is greater than the distal one).

It is a second object of the present invention to provide an inflatable cuff which can be used for a long period of time without producing congestive marks in the skin of a body portion of a living body around which the cuff is wound.

According to a second aspect of the present invention, there is provided an inflatable cuff for pressing a body portion of a living subject by being wound and inflated around the body portion, in measuring a blood pressure of the subject, the cuff comprising (a) a pressing bag having a fluid-tight space therein; and (b) an inflatable bag having an inflatable chamber therein, the inflatable bag being provided in the fluid-tight space of the pressing bag such that a fluid is left outside the inflatable bag and inside the pressing bag.

In the inflatable cuff in accordance with the second aspect of the invention, a pressurized fluid is supplied to the inflatable bag with the cuff being wound around the body portion of the subject, so that the inflatable bag is inflated to press the body portion. Since the inflatable bag is provided in the fluid-tight space such that a fluid is left outside the inflatable bag and inside the pressing bag, the fluid moves from an outer section of the fluid-tight space to an inner section of the same upon inflation of the inflatable cuff. Therefore, even if the corrugation of an inner portion of the inflatable bag produced when the cuff is wound around the body portion of the subject, is deformed into acute wrinkles upon inflation of the inflatable bag, an inner portion of the pressing bag is effectively prevented from being so deformed as to comply with the deformation of the inflatable bag, because of the above-mentioned movement of the fluid. Thus, the skin of the body portion of the subject is prevented from being pinched by the pressing bag, and the present cuff may be used for a long period of time in repetitively measuring blood pressure values of the subject, with less discomfort of the subject, e.g., without producing congestive marks in the skin of the subject.

According to a third aspect of the present invention, there is provided an inflatable cuff for pressing a body portion of a living subject by being wound and inflated around the body portion, in measuring a blood pressure of the subject, the cuff comprising (a) an inner portion which is adapted to contact the body portion of the subject when the cuff is wound around the body portion; and (b) an outer portion which cooperates with the inner portion to provide a pressing bag adapted to press the body portion of the subject, the outer portion being formed of a material having an elasticity such that the outer portion is elastically deformable up to a prescribed maximum amount when the cuff is inflated around the body portion.

In the inflatable cuff in accordance with the third aspect of the invention, the outer portion is formed of an elastic material. When the pressing bag of the cuff wound around the body portion of the subject is inflated to press the body portion, the outer portion is elastically elongatable up to a small upper-limit amount in a circumferential direction of the cuff. Therefore, the the inner portion of the pressing bag is effectively prevented from being corrugated because of the difference between the respective diameters of the inner and outer portions when the cuff is wound around the body portion. Accordingly, the production of acute wrinkles from the corrugation is minimized. Thus, the skin of the body portion of the subject is protected from being pinched by the pressing bag, and the present cuff may be used for a long period of time in repetitively measuring blood pressure values of the subject, with less discomfort of the subject, e.g., without producing congestive marks in the skin of the subject.

It is a third object of the present invention to provide an inflatable cuff which has an original width appropriate for some living subjects and is adjustable to have an adjusted width appropriate for other living subjects having a characteristic different from that of the first living subjects.

According to a fourth aspect of the present invention, there is provided an inflatable cuff for pressing a body portion of a living subject by being wound and inflated around the body portion, in measuring a blood pressure of the subject, the cuff comprising (a) an inflatable bag having an inflatable chamber therein; and (b) a width adjustment device for adjusting a width of the inflatable chamber in a direction parallel to a center line of the cuff cylindrically wound around the body portion of the subject.

In the inflatable cuff in accordance with the fourth aspect of the present invention, the width of the inflatable chamber is adjustable depending upon, for example, the circumferential length of the body portion of the subject around which the cuff is wound. Therefore, the present cuff can be used for a plurality of living subjects having different characteristics for which it is appropriate to use different cuffs having different widths. Thus, the present cuff may be used widely.

It is a fourth object of the present invention to provide an inflatable cuff including an inflatable bag which does not break upon inflation thereof when the cuff is not in use off a body portion of a living subject.

According to a fifth aspect of the present invention, there is provided an inflatable cuff for pressing a body portion of a living subject by being wound and inflated around the body portion, in measuring a blood pressure of the subject, wherein the improvement comprises an inflatable bag having an inflatable chamber therein, and formed by fluid-tightly sealing a pair of sealing portions of an elastic sheet to each other, the pair of sealing portions having a predetermined with along an outer periphery of the elastic sheet, and including a pair of non-sealing areas which cooperate with each other to define a relief channel which, when the cuff is not in use off the body portion of the subject, does not open before a fluid pressure in the inflatable chamber exceeds a reference value and opens when the fluid pressure of the inflatable chamber exceeds the reference value.

In the inflatable cuff in accordance with the fifth aspect of the present invention, the two portions of the elastic sheet constituting the inflatable bag are separated from each other when a pressurized fluid is supplied to the inflatable bag to start inflation of the inflatable bag. In this situation, the two non-sealing areas defining the relief channel are held in contact with each other because of a tensile force produced in a longitudinal direction of the sealing portions and an elastic force of the elastic sheet. That is, the relief channel remains closed. However, as the fluid pressure of the inflatable bag increases, the pressurized fluid flows into the relief channel so as to reduce little by little the area of contact of the two non-sealing areas. When the fluid pressure of the inflatable bag (i.e., fluid pressure in the inflatable chamber) exceeds a reference value, the pressurized fluid starts leaking through the relief channel, thereby preventing the inflatable bag from being inflated any more. The reference pressure value may be predetermined depending upon the width of the sealing portions, the length of the non-sealing areas (the direction of length of the non-sealing areas is perpendicular to the direction of width of the sealing portions), and the elasticity of the inflatable bag (i.e., elasticity of the elastic sheet). By selecting appropriate values of those parameters, the fluid pressure of the inflatable bag can be controlled not to exceed the upper limit value below which the inflatable bag does not break upon inflation thereof. Thus, the present cuff can be removed from the body portion of the subject, without taking it into considerations that the inflatable bag may break upon inflation of the inflatable bag when the cuff is not in use off the body portion.

In a preferred embodiment in accordance with the fifth aspect of the invention, the inflatable cuff further comprises a pressing bag having an inner space therein, the inflatable bag being provided in the inner space of the pressing bag. In this case, when the cuff is in use being wound around the body portion of the subject, the amount of inflation of the inflatable bag is appropriately controlled by the pressing bag enclosing the inflatable bag, so that the area of contact of the non-sealing areas is not reduced to below a reference value and accordingly the pressurized fluid is prevented from leaking from the inflatable chamber or bag. Thus, the provision of the relief channel in the present cuff does not result in adversely influencing the reliability of blood pressure measurements using the cuff.

It is a fifth object of the present invention to provide an inflatable cuff which prevents the skin of a living subject from becoming sweaty or sodden in the case where the cuff is wound around a body portion of the subject for a long period of time.

According to a sixth aspect of the present invention, there is provided an inflatable cuff for pressing a body portion of a living subject by being wound and inflated around the body portion, in measuring a blood pressure of the living subject, the cuff comprising (a) an outer sheet member; and (b) an inner sheet member which cooperates with the outer sheet member to provide a pressing bag adapted to press the body portion of the subject, at least a portion of the inner sheet member including (b1) a first layer formed of a multiplicity of fibers, the first layer having a first major surface adapted to directly contact the body portion of the subject when the cuff is wound around the body portion, and (b2) a second layer formed of a resin film, the second layer being fixed to a second major surface of the first layer to prevent a fluid from leaking from the pressing bag through the first layer, the second major surface being opposite to the first major surface.

In the inflatable cuff in accordance with the sixth aspect of the invention, at least a portion of the inner sheet member includes the first fibrous layer adapted to directly contact the skin of the subject and the second resin layer fixed to the first fibrous layer to prevent a fluid such as an air from leaking from the pressing bag. Since air is permitted to flow through fine spaces between the fibers of the fibrous layer held in contact with the subject's skin with the cuff being wound around the body portion, the subject's skin is kept dry and thus prevented from becoming sweaty or sodden. In addition, since the inner sheet member of the present cuff is not provided with a flexible bag having a number of air holes through which air comes out, disclosed in Unexamined Japanese Utility Model Application laid open under Publication No. 62-170002, the cuff can be wound around the body portion with a substantially uniform pressing force over the entire circumferential length of the body portion such as an upper arm. Thus, the accuracy of blood pressure measurements using the cuff is not lowered.

According to a seventh aspect of the present invention, there is provided an inflatable cuff for pressing a body portion of a living subject by being wound and inflated around the body portion, in measuring a blood pressure of the living subject, the cuff comprising (a) an outer sheet member; and (b) an inner sheet member which cooperates with the outer sheet member to provide a pressing bag adapted to press the body portion of the subject, at least a portion of the inner sheet member including (b1) a first layer formed of a porous resin film which permits an air to slightly flow from the pressing bag therethrough, and (b2) a second layer formed of a multiplicity of fibers, and provided on the first layer, the second layer being adapted to directly contact the body portion of the subject when the cuff is wound around the body portion.

In the inflatable cuff in accordance with the seventh aspect of the present invention, at least a portion of the inner sheet member includes the first porous layer which permits an air to slightly flow from the pressing bag therethrough, and the second fibrous layer provided on the first porous layer and adapted to directly contact the body portion of the subject. When the pressing bag is inflated during a blood pressure measurement period, the air slightly flows out of the pressing bag through the inner sheet member. Since the air flows through fine spaces between the fibers of the fibrous layer held in contact with the subject's skin with the cuff being wound around the body portion, the subject's skin is kept dry and thus prevented from becoming sweaty or sodden. In addition, since the inner sheet member of the present cuff is not provided with a flexible bag disclosed in the above-identified Japanese Utility Model Application, the cuff can be wound around the body portion with a uniform pressing force over the entire circumferential length of the body portion. The accuracy of blood pressure measurements using the cuff is not lowered.

According to an eighth aspect of the present invention, there is provided an inflatable cuff for pressing a body portion of a living subject by being wound and inflated around the body portion, in measuring a blood pressure of the living subject, the cuff comprising (a) an outer sheet member; (b) an inner sheet member which cooperates with the outer sheet member to provide a pressing bag adapted to press the body portion of the subject; (c) a resin sheet which is formed of a resin which absorbs a water, and provided on the inner sheet member; and (d) a porous sheet which is formed of a porous material, provided on the resin sheet, and fixed to the inner sheet member to support the resin sheet, the porous sheet being adapted to directly contact the body portion of the subject when the cuff is wound around the body portion.

In the inflatable cuff in accordance with the eighth aspect of the present invention, the water-absorbing resin sheet and the porous sheet are provided on the inner sheet member. Therefore, the moisture or water coming out from the subject's skin held in contact with the inner sheet member of the cuff passes through the porous sheet and is absorbed by the resin sheet. Thus, the subject's skin is effectively prevented from becoming sweaty or sodden. In addition, since the inner sheet member of the present cuff is not provided with a flexible bag disclosed in the above-identified Japanese Utility Model Application, the cuff can be wound around the body portion with a uniform pressing force over the entire circumferential length of the body portion. Therefore, the accuracy of blood pressure measurements using the cuff is not lowered.

It is a sixth object of the present invention to provide an automatic blood pressure measuring apparatus including an inflatable cuff, which apparatus prevents the skin of a living subject from becoming sweaty or sodden when the cuff is wound around a body portion of the subject for a long period of time.

According to a ninth aspect of the present invention, there is provided an automatic blood pressure measuring apparatus, comprising (a) an inflatable cuff adapted to be wound around a body portion of a living subject; (b) a pressure regulating device which regulates a fluid pressure in the cuff to press the body portion of the subject; (c) a heartbeat-synchronous wave sensor which detects a heartbeat-synchronous wave produced from the body portion of the subject in synchronism with heartbeat of the subject, while the fluid pressure of the cuff is changed by the pressure regulating device; (d) determining means for determining a blood pressure of the subject based on the heartbeat-synchronous wave detected by the heartbeat-synchronous wave sensor; (e) a vacuum producing device which produces a vacuum whose pressure is lower than an atmospheric pressure under which the cuff is used; and (f) a cuff deflating device which communicates the cuff with the vacuum producing device after the blood pressure of the subject has been determined by the determining means, and forcibly deflates the cuff by discharging a fluid from the cuff because of the vacuum produced by the vacuum producing device.

In the automatic blood pressure (BP) measuring apparatus constructed as described above, the cuff deflating device communicates the cuff with the vacuum device after determination of the BP value of the subject, and forcibly deflates the cuff. Thus, the cuff is loosened around the body portion of the subject, so that the area of contact of the cuff with the skin of the body portion is minimized. Consequently, the amount of air permitted to flow through the space between the cuff and the subject's skin is greatly increased, so that the skin is effectively prevented from becoming sweaty or sodden.

In a preferred embodiment in accordance with the ninth aspect of the present invention, the inflatable cuff comprises an outer sheet member; and an inner sheet member which cooperates with the outer sheet member to provide a pressing bag adapted to press the body portion of the subject, at least a portion of the inner sheet member including a first layer formed of a porous resin film which permits an air to slightly flow from the pressing bag therethrough, and a second layer formed of a multiplicity of fibers and provided on the first layer, the second layer being adapted to directly contact the body portion of the subject when the cuff is wound around the body portion. In this case, ambient air is sucked through fine spaces between the fibers of the second fibrous layer, into the pressing bag. Thus, the subject's skin held in contact with the pressing bag is more effectively kept dry and prevented from becoming sweaty or sodden.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 7 is a view showing two deformed states of an inner portion of the cuff of FIG. 1 when the cuff is used in the first manner shown in FIG. 5, including a left-hand half corresponding to a deflated state of the cuff and a right-hand half corresponding to an inflated state of the cuff;

FIG. 9 is a view corresponding to the right-hand half of FIG. 7, showing an inflated state of a conventional inflatable cuff;

FIG. 10 is a plan view of an inner surface of another inflatable cuff as a second embodiment of the present invention;

DETAILED DESCRIPTION OF THE PREFERRED EMBODIMENTS

Figure 1:
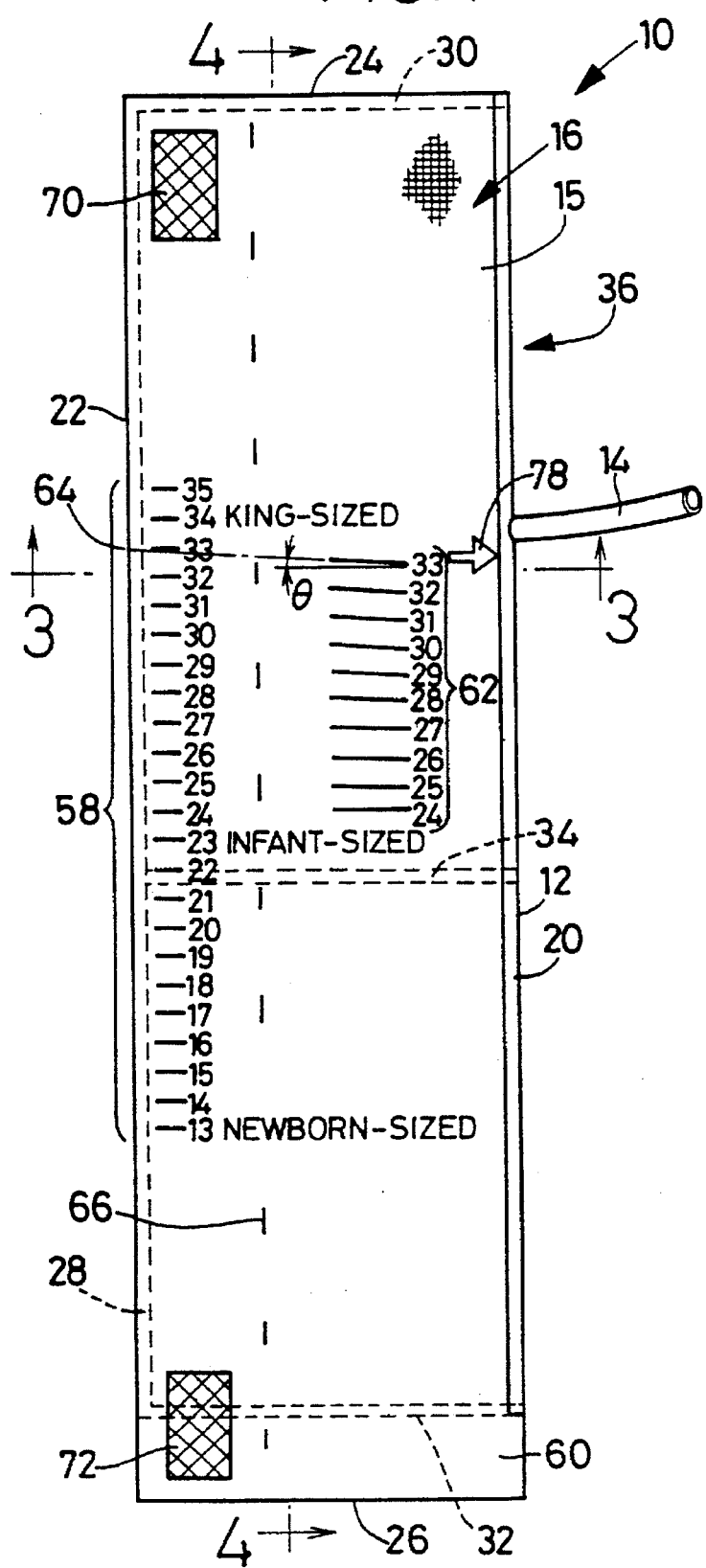
FIG. 1 is a plan view of an outer surface of an inflatable cuff embodying the present invention.
Figure 2:
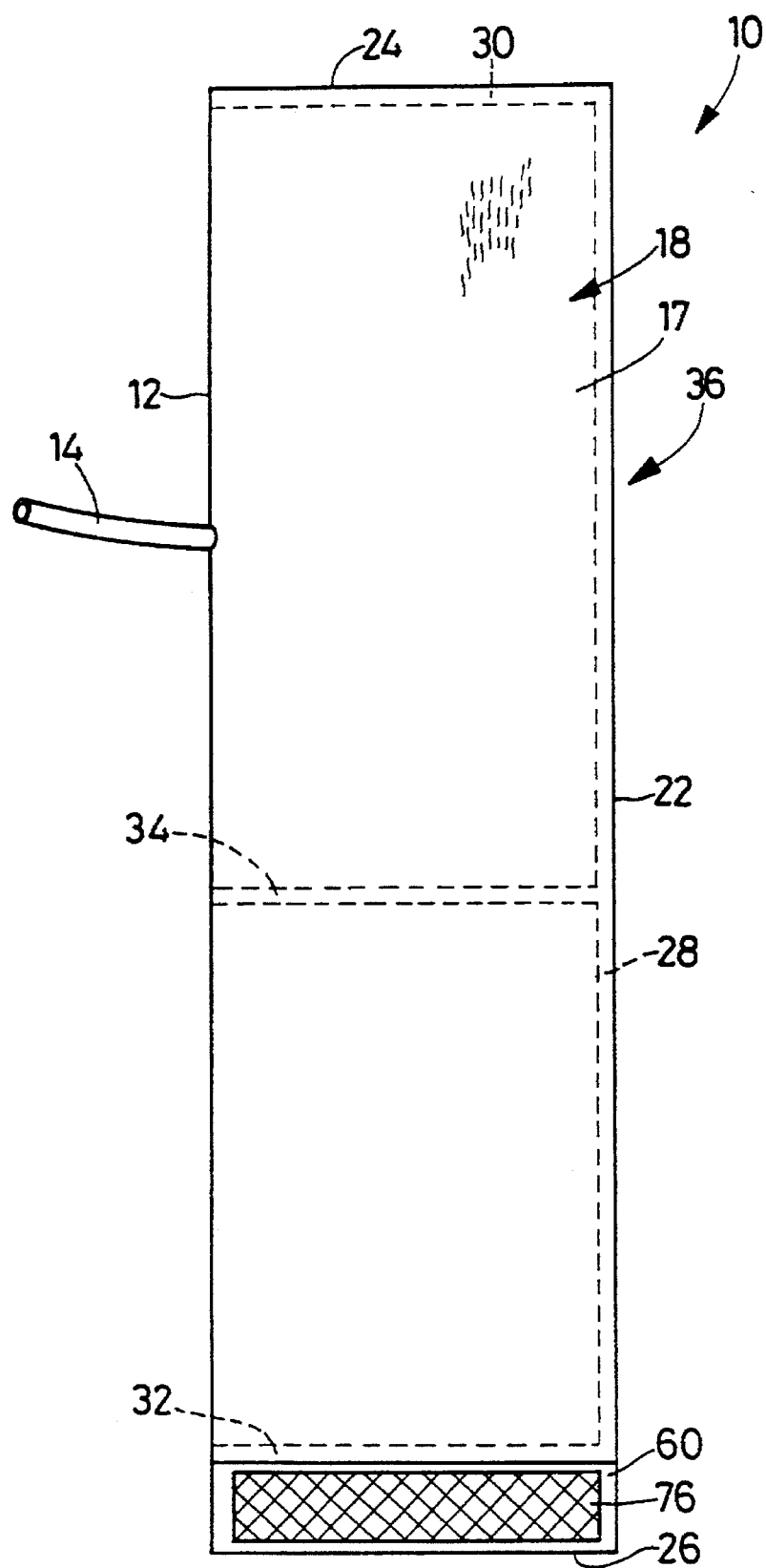
FIG. 2 is a plan view of an inner surface of the cuff of FIG. 1.
Figure 3:
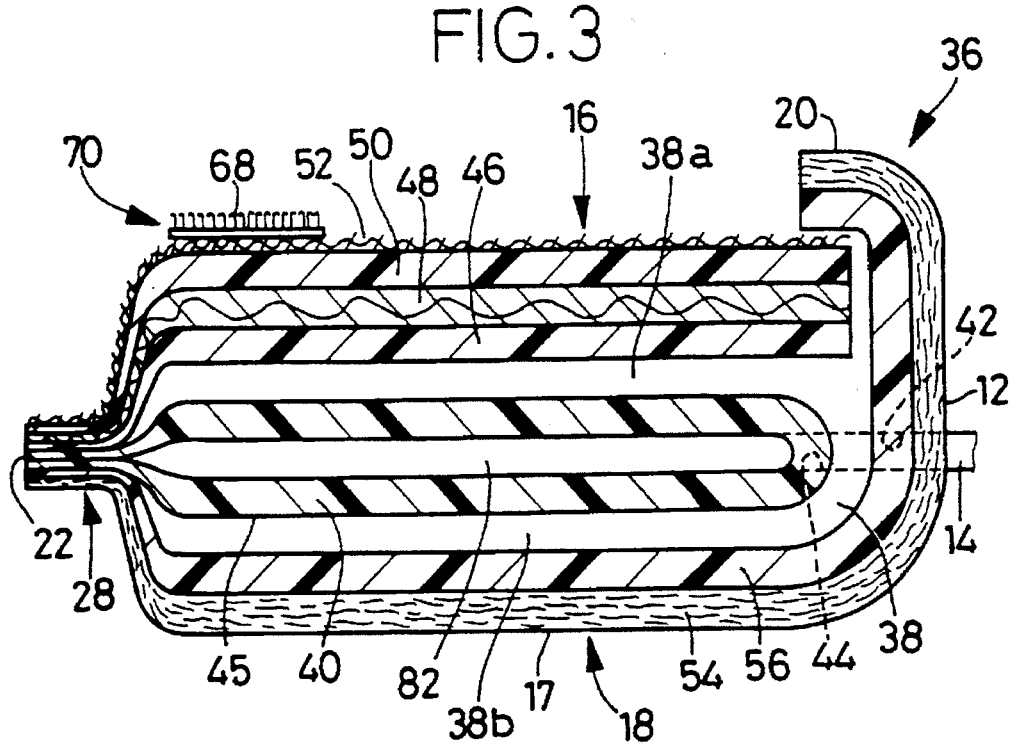
FIG. 3 is an illustrative, transverse cross-sectional view of the cuff of FIG. 1 taken along Line 3—3 of FIG. 1.
Figure 4:
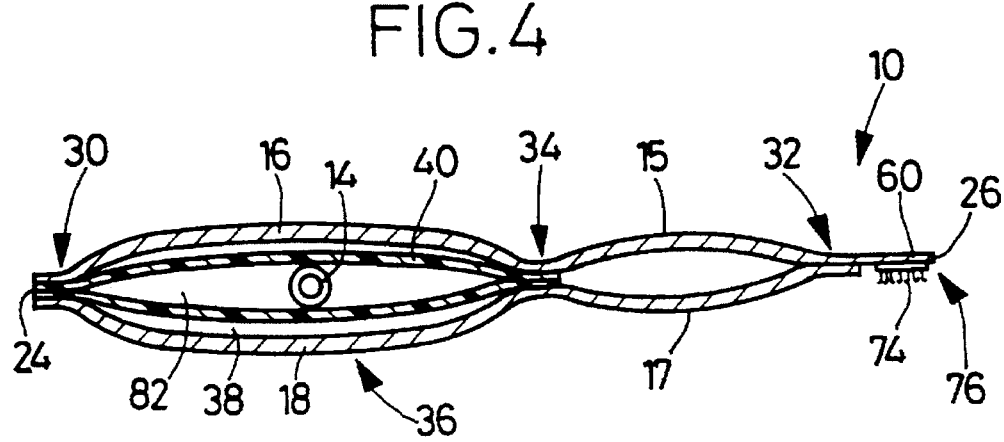
FIG. 4 is an illustrative, longitudinal cross-sectional view of the cuff of FIG. 1 taken along Line 4—4 of FIG. 1.
Figure 5:
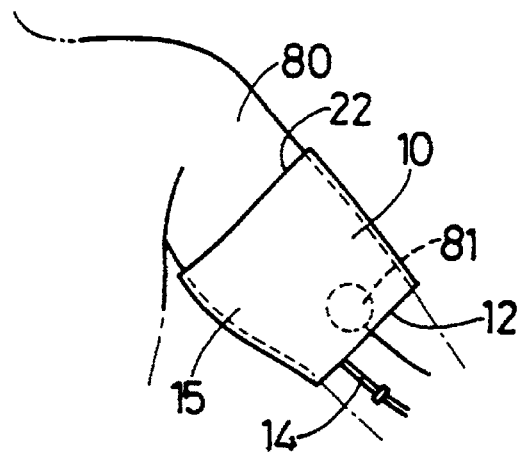
FIG. 5 is a view showing a manner of use of the cuff of FIG. 1.

Referring to FIG. 1, there is shown an inflatable cuff 10 for use in measuring a blood pressure of a living subject such as a patient. FIG. 1 shows an outer major surface 15 of the cuff 10. As shown in FIG. 5, the outer surface 15 is exposed when the cuff 10 is wound around a body portion of the subject, such as an upper arm 80, so that the outer surface 15 can be seen by a user such as a doctor or nurse. FIG. 2 shows an inner major surface 17 of the cuff 10. The inner surface 17 is not exposed or visible, and contacts the arm 80, with the cuff 10 being wound around the arm 80. FIG. 3 shows a transverse cross-sectional view of the cuff 10 taken along Line 3—3 of FIG. 1, and FIG. 4 is a longitudinal cross-sectional view of the cuff 10 taken along Line 4—4 of FIG. 1.

Figure 15:
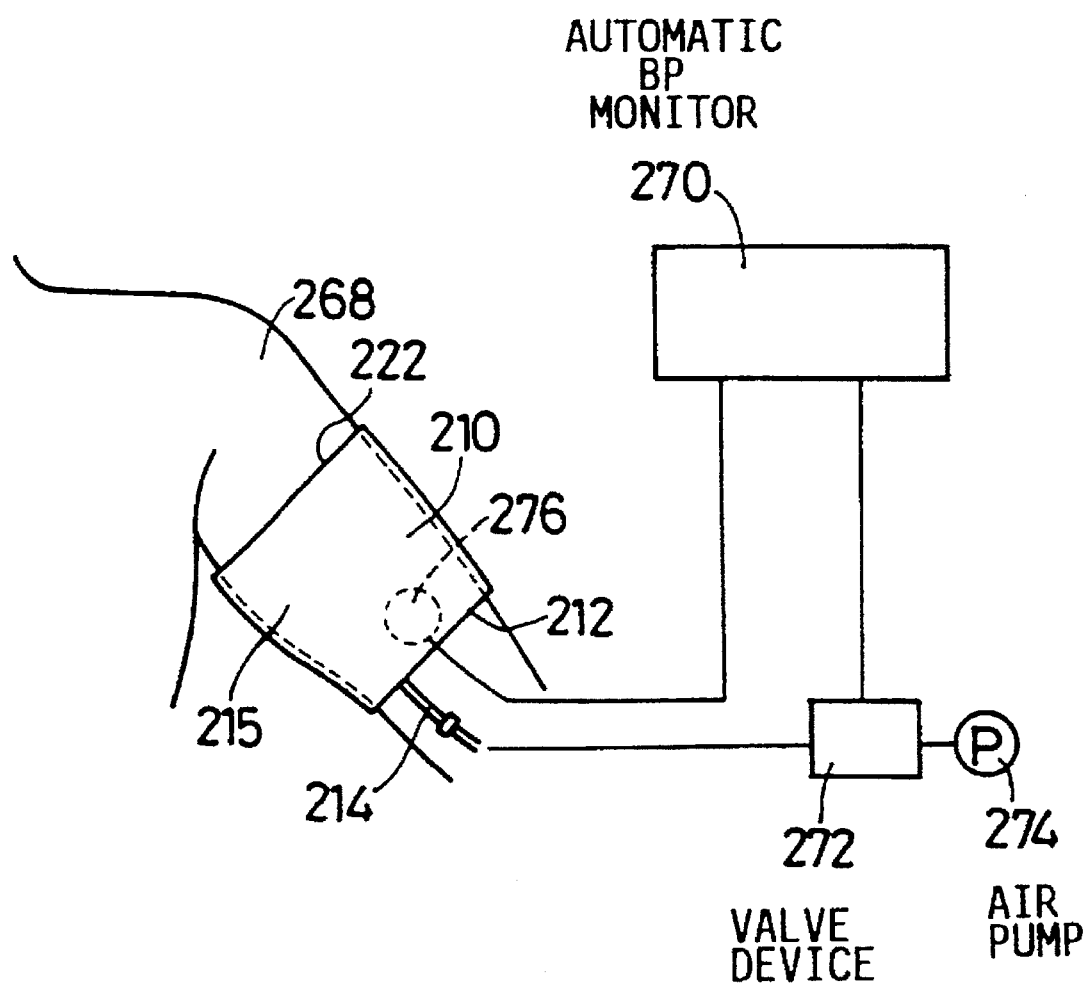
FIG. 15 is a view showing a manner of use of the cuff of FIG. 10.
Figure 21:
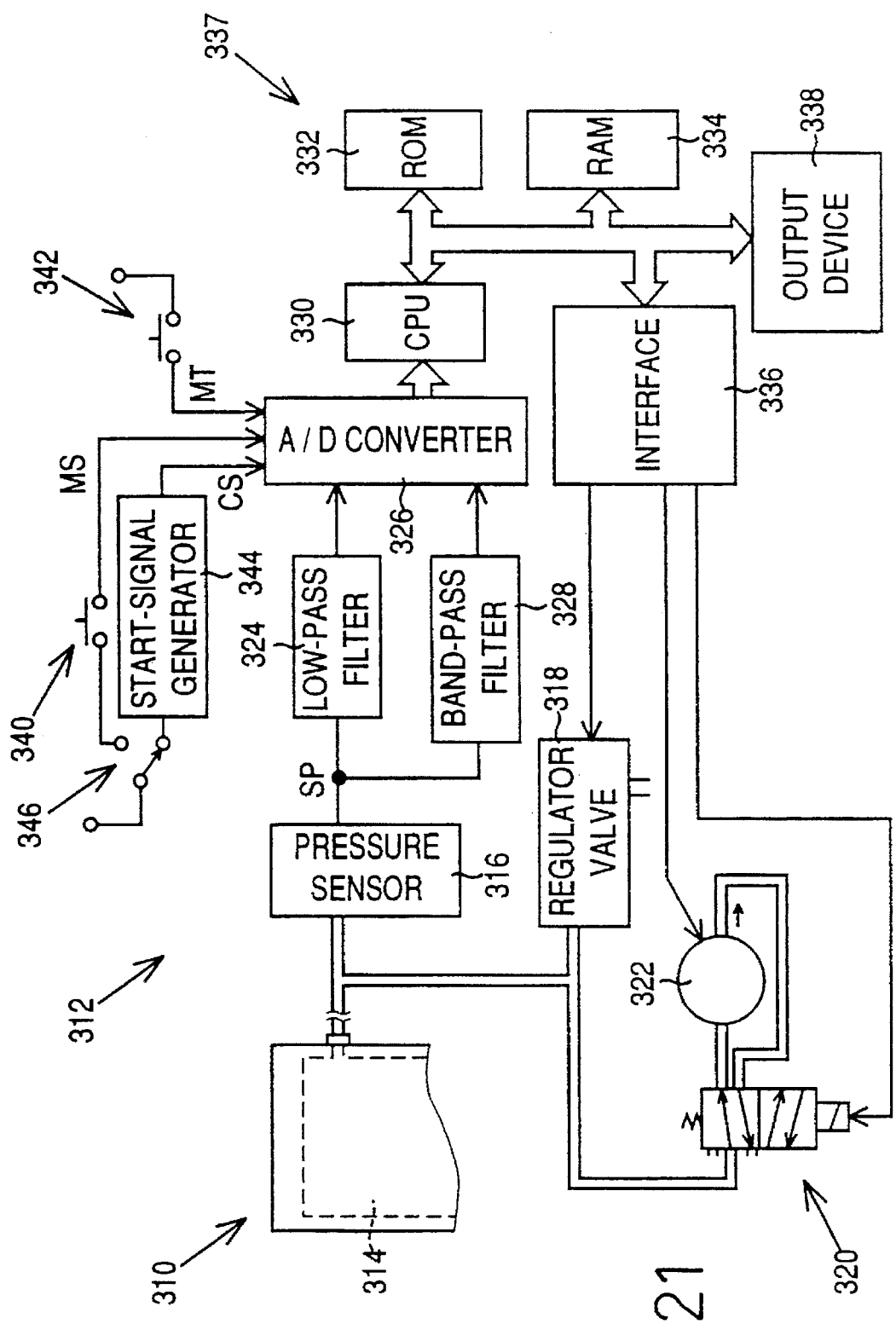
FIG. 21 is a diagrammatic view of an automatic blood pressure measuring apparatus including the cuff of FIG. 16.

The cuff 10 has a belt-like configuration with an about 50 cm length, an about 14 cm width, and an about 1.5 mm thickness. As shown in FIG. 5, an air pipe 14 is connected to a distal long edge 12 of the cuff 10. The distal long edge 12 is more distant from the heart of the subject, than an opposite, proximal long edge 22, with the cuff 10 being wound around the arm 80. The cuff 10 is connected via the air pipe 14 to a pressurized-air supplying and discharging device (not shown), when the cuff 10 is used in measuring a blood pressure value of the patient. The cuff 10 may be used with an automatic blood pressure measuring device as shown in FIG. 15 or FIG. 21.

The cuff 10 includes an outer member 16 defining the outer surface 15, and an inner member 18 defining the inner surface 17. As shown in FIG. 3, the inner member 18 is folded back to provide a folded portion 20 along the distal long edge 12 of the cuff 10. The inner member 18 is adhered to the outer member 16 at the folded portion 20 along the distal long edge 12. In addition, the inner and outer members 18, 16 have a first, a second, and a third sealing portion 28, 30, 32 along the proximal long edge 22 and a first and a second short edge 24, 26, respectively, and a fourth sealing portion 34 extending parallel to the opposite short edges 24, 26 at an intermediate location in the longitudinal direction of the cuff 10. The inner and outer members 18, 16 are bonded to each other by thermocompressing the four sealing portions 28, 30, 32, 34, so that a pressing bag 36 is provided which has an air-tight inner space 38 defined by the folded portion 20 and the sealing portions 28, 30, 34.

As shown in FIG. 3, an inflatable bag 40 is provided in the inner space 38 of the pressing bag 36 of the cuff 10. The inflatable bag 40 is air-tightly constructed by folding a resin sheet along the distal long edge 12 and subsequently thermocompressing the sheet at respective open edges thereof corresponding to the sealing portions 28, 30, 34 of the inner and outer members 18, 16 simultaneously with the thermocompressing of the two members 18, 16. The resin sheet used for the bag 40 is, for example, an ethylene-vinyl acetate (EVA) resin film formed of a composition containing 15 to 20% of vinyl acetate and 85 to 80% of linear low-density polyethylene (LDPE), and having an about 0.02 mm thickness. This resin film possesses a high tensile strength and a high elongation. It is preferred that the inflatable bag 40 be finished to have a multiplicity of fine bosses in a major surface 45 thereof which is to contact respective inner layers 56, 46 of the inner and outer members 18, 16.

The inner member 18 and the inflatable bag 40 have respective through-holes 42, 44 through which the air pipe 14 is inserted to communicate an inflatable chamber 82 in the bag 40 with the air supplying and discharging device (not shown). The air pipe 14 is air-tightly fixed to the inner member 18 and the bag 40 by thermocompressing. The major surface 45 of the bag 40 is not entirely fixed, that is, is displaceable relative to the inner and outer members 18, 16, except for the respective edge portions thereof corresponding to the sealing portions 28, 30, 34 and the through-hole 44 that is fixed to the inner member 18 via the air pipe 14. An appropriate amount of air is left in the air-tight inner space 38 of the pressing bag 36. As shown in FIG. 4, the inflatable bag 40 extends from the second sealing portion 30 to the fourth sealing portion 34, but does not extend into a vacant space defined by the folded portion 20 and the sealing portions 28, 32, 34.

The outer member 16 has a four-layer integral structure including (a) an innermost or first layer 46 formed of a polyethylene resin and having an about 0.04 mm thickness; (b) a second layer 48 formed of a cloth woven using fibers of a polyethylene from a medium or low pressure polymerization process, at a weaving density of 10×10/inch; (c) a third layer 50 formed of the same material as that of the first layer 46; and (d) an outermost or fourth layer 52 formed of a nylon pile produced in a 40/20 yarn usage, having a weight of 65 g/m², and including fibers finely corrugated in the longitudinal direction of the cuff 10 and a multiplicity of looped fibers exposed in the outer surface 15. Because of the use of the fibers corrugated in the cuff's longitudinal direction in the outermost layer 52 and the use of the polyethylene resin in the third layer 50, the outer member 16 has an elasticity which permits the cuff 10 to be elastically deformed up to a small maximum amount or length in the cuff's longitudinal direction. The first and second layers 46, 48 are employed for increasing the tensile strength of the outer member 16, thereby preventing the member 16 from breaking when the bag 40 is inflated and accordingly the member 16 is elongated around the arm 80.

The inner member 18 has a two-layer integral structure including (a) an outer layer 54 formed of a non-woven cloth produced using a 50% rayon, 50% polyester blended yarn, and having a weight of 60 g/m² and an about 0.55 mm thickness; and (b) an inner or lining layer 56 formed of a polyethylene resin and having an about 0.05 mm thickness. The inner member 18 cooperates with the outer member 16 to provide the air-tight inner space 38 of the pressing bag 36. Because of the use of the non-woven cloth in the outer layer 54 and the use of the polyethylene resin in the lining layer 56, the inner member 18 has an elasticity in the cuff's longitudinal direction. Therefore, when an pressurized air is supplied to the inflatable bag 40 and the air pressure in the inner space 38 of the pressing bag 36 increases up to 250 to 300 mmHg, the outer member 16 is elongated by a sufficient amount to prevent acute wrinkles from being produced in the inner member 18 in the cuff's transverse direction due to the difference between respective diameters of the two members 16, 18 with the cuff 10 being wound around the arm 80. In FIGS. 3 and 4, the respective elements or parts of the cuff 10 are not illustrated with their accurate dimensions relative to each other, but for illustrative purposes only.

Back to FIG. 1, the outer member 16 has, on the outer surface 15 (i.e., outer surface of the outermost layer 52), measurement graduations 58 along a predetermined, intermediate length of the proximal long edge 22. In the present embodiment, the measurement graduations 58 include twenty-three short straight segments graduated in centimeters, each perpendicular to the edge line 22, and twenty-three numbers, "13" to "35", associated with the respective short segments. A circumferential length of the upper arm 80 around which the cuff 10 is wound, is measured in centimeters by reading a number "13" to "35" associated with a short segment aligned with the second short edge 26 with the cuff 10 being cylindrically wound around the arm 80 such that an end portion 60 including the short edge 26 is superposed on the outer surface 15.

In addition, the outer member 16 has, on the right-hand side of the measurement graduations 58 in FIG. 1 and at an almost middle and slightly right-sided position in the cuff's transverse direction, cuff-winding graduations 62 including short straight segments numbered "24" to "33" corresponding to the short segments numbered "24" to "33" of the measurement graduations 58. The short segments "25" to "33" of the cuff-winding graduations 62 are inclined by different angles, Θ, with respect to the corresponding short segments "25" to "33" of the measurement graduations 58. As the numbers increase from "25" to "33", the inclination angles Θ of the inclined short segments of the cuff-winding graduations 62 increase. The short segment "24" of the cuff-winding graduations 62 is not inclined, i.e. is flush, with the corresponding short segment "24" of the measurement graduations 58. A prolongation line of each of the inclined short segments of the cuff-winding graduations 62 intersects a prolongation line of a corresponding one of the short segments of the measurement graduations 58, on the proximal long edge 22. Regarding the two short segments numbered "33", for example, the two prolongation lines thereof intersect each other at a point 64, as illustrated in one-dot chain line in FIG. 1.

Between the measurement graduations 58 and the cuff-winding graduations 62, a folding-position line 66 is provided which extends from the first short edge 24 to the second short edge 26, parallel to the proximal long edge 22, and distant by about 8 to 9 cm from the distal long edge 12. In the longitudinally opposite end portions of the cuff 10 between the proximal long edge 22 and the folding-position line 66, a first and a second fastener pad 70, 72 are provided each of which includes a multiplicity of hooks 68, as shown in FIG. 3, like one of a pair of magic tapes in accordance with Japanese Industrial Standard (JIS) L0213. On an opposite surface of the end portion 60, a third fastener pad 76 is provided which includes a multiplicity of hooks 74, as shown in FIG. 4, like the pads 70, 72. The third pad 76 covers all over the opposite surface of the end portion 60.

An arrow 78 provided on the outer surface 15 is utilized such that when the cuff 10 is wound around the arm 80, the arrow 78 is aligned with a brachial artery of the patient. The measurement graduations 58, cuff-winding graduations 62, folding-position line 66, and arrow 78 are provided by printing directly on the outer surface of the outermost layer 52 of the outer member 16.

Hereinafter, there will be described, by reference to FIG. 5, the method of winding the inflatable cuff 10 constructed as described, around a body portion of a living subject such as an upper arm 80 of a patient, in measuring a blood pressure of the patient.

First, the circumferential length of the upper arm 80 is measured by using the measurement graduations 58 provided on the outer surface 15 of the cuff 10. The cuff 10 is wound around the arm 80 in such a manner that the proximal long edge 22 is positioned on the side of the shoulder, the distal long edge 12 to which the air pipe 14 is connected is positioned on the side of the elbow, the outer surface 15 is externally exposed, and the winding is started with the first short edge 24 and ended with the second short edge 26. For accurately measuring the circumferential length of the arm 80, the winding of the cuff 10 around the arm 80 is carried out such that the diameter of winding of the proximal edge 22 is the same as that of the distal edge 12, i.e., such that the entire length of the proximal edge 22 is positioned in one plane and the entire length of the distal edge 12 is positioned in another plane parallel to the first plane. One of the measurement graduations 58 which is aligned with the second short edge 26 in this situation is read as the measured value of the circumferential length of the arm 80. If the measured value falls within the range of 24 to 33 cm, the cuff 10 is adjusted around the arm 80 by fixing the proximal end of the second short edge line 26, unchanged, and simultaneously changing the diameter of winding of the distal edge 12, so that the second short edge 26 is aligned with a prolongation line of one of the cuff-winding graduations 62 (e.g., one-dot chain line drawn from the inclined short segment numbered "33" (cm) in FIG. 1) which corresponds to one of the measurement graduations 58 which indicates the measured circumferential length of the arm 80. This alignment is secured by pressing the cuff-winding fastener pad 76 onto the outermost layer 52 of the outer member 16. Additionally, the cuff 10 is wound around the arm 80 such that the arrow 78 is aligned with the brachial artery of the patient. The latter alignment is effected likewise also in the case where the measured circumferential length of the arm 80 falls within the range of 14 to 23 cm. In FIG. 5, reference numeral 81 designates a microphone for detecting Korotkoff sounds produced from the brachial artery.

In the case where the measured circumferential length is greater than 33 (cm) or smaller than 14 (cm), the cuff 10 is not appropriate for use in measuring the blood pressure of that patient. In this case, another cuff of a different size is used. The indication, "KING-SIZED", provided on the right-hand side of the graduation numbered "34" suggests that the arm in question is too thick, or the width of the cuff 10 (that is equal to the length of the edge line 24, 26) is too small, and accordingly an accurate blood pressure measurement is not feasible and that another cuff of a king size should be used in place of the cuff 10. Likewise, the indication, "NEWBORN-SIZED", provided on the right-hand side of the graduation numbered "13" suggests that the arm is too thin, or the width of the cuff 10 is too great, and accordingly an accurate blood pressure measurement is not feasible and that another cuff of a newborn size should be used in place of the cuff 10.

Figure 6:
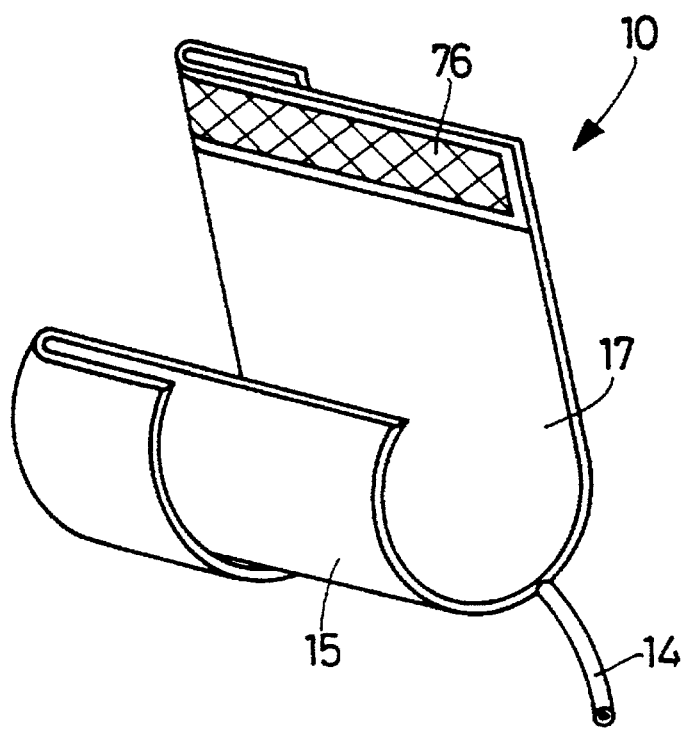
FIG. 6 is a view showing another manner of use of the cuff of FIG. 1.

If the measured circumferential length of the arm 80 falls within the range of 14 to 23 cm, the width of the cuff 10 is excessively great. In this case, the cuff 10 is folded back at the folding-position line 66 and the cuff-folding fastener pads 70, 72 are pressed onto the outer surface 15, so that the width of the cuff 10 is reduced to the length between the distal edge line 12 and the folding-position line 66, i.e., to about 8 to 9 cm, as shown in FIG. 6. Since each of the fastener pads 70, 72, 74 has a multiplicity of hooks 68 or 74, the tips of the hooks 68, 74 are held in engagement with the nylon pile, i.e., looped fibers of the outermost layer 52. Thus, the cuff 10 wound around the arm 80 is securely fixed relative to the arm 80.

With the cuff 10 being wound around the arm 80, a pressurized air is supplied from the air supplying and discharging device (not shown) to the inflatable chamber 82 of the inflatable bag 40 via the air pipe 14, so that the bag 40 is inflated and accordingly the inner surface 17 is moved inwardly as shown in FIG. 7. Consequently, the arm 80 is pressed, and blood pressure values of the patient are measured by a known blood pressure measuring method. In FIG. 7, the arm 80 is not shown. The left-hand half of FIG. 7 shows the cuff 10 in a deflated state thereof, while the right-hand half shows the cuff 10 in an inflated state thereof.

It emerges from the foregoing description that in the present embodiment the circumferential length of the upper arm 80 is measured with the measurement graduations 58 provided along the proximal long edge 22 when the cuff 10 is wound around the arm 80 in measuring a blood pressure of the patient and the cuff 10 is fixed on the arm 80 according to one of the cuff-winding graduations 62 corresponding to the measured circumferential length. Consequently, the arm 80 is pressed by the cuff 10 with an appropriate pressure over the entire circumferential length of the arm 80. Thus, the cuff 10 can be wound around the arm 80 in an appropriate manner without needing the skill of a user. With the present cuff 10, reliable accurate blood pressure measurements can easily be effected.

Generally, a thicker upper arm 80 has a greater difference between the circumferential length of the arm 80 measured at the proximal long edge 22 and that measured at the distal long edge 12 (the former is greater than the latter). Based on this knowledge, the inclination angles $\Theta$ of the respective short segments 62 are so graduated as to increase as the numbers associated therewith increase from "24" to "33". An accurate blood pressure measurement cannot be effected if the cuff 10 is not wound around the arm 80 with a uniform pressing force over the entire circumferential length of the arm 80. In the case where the cuff 10 is used, as shown in FIG. 5, on a thick upper arm 80 having a great difference between the respective circumferential lengths of the arm 80 measured at the proximal and distal long edges 22, 12, it is required that the cuff 10 be wound around the arm 80 so as to have the shape of a truncated cone to comply with the profile of the arm 80 and thereby press the arm 80 with a uniform pressing force over the entire circumferential length of the arm 80. Concerning a conventional inflatable cuff, the winding of the cuff around the body portion such as the upper arm 80 needs the skill of a user. However, in the present embodiment, the cuff 10 having the above-described structural features is easily wound around even the thick arm 80 without needing the skill of a user. In the present embodiment, the cuff 10 does not have cuff-winding graduations 62 corresponding to smaller than 24 cm measurement graduations 58. However, generally, a thin upper arm having such a small circumferential length has only a small difference between the respective circumferential lengths measured at the proximal and distal long edges 22, 12, and the winding of the cuff 10 around the thin arm is not difficult.

In the present embodiment, the inflatable bag 40 is provided in the air-tight inner space 38 defined by the inner and outer members 18, 16, such that the outer surface 45 of the bag 40 is displaceable relative to the two members 18, 16. A pressurized air is supplied to the inflatable bag 40. When the cuff 10 is wound around the arm 80 in measuring a blood pressure of the patient, the cuff 10 is first put in the deflated state thereof as shown in the left-hand half of FIG. 7 in which the inner portion 17 of the inner member 18 and an inner portion 83 of the inflatable bag 40 are corrugated in the circumferential direction of the arm 80. When the cuff 10 is inflated into the inflated state thereof as shown in the right-hand half of FIG. 7, the inflatable bag 40 is inflated so that the corrugation of the inner portion 83 of the bag 40 changes into acute wrinkles.

FIG. 9 shows a conventional inflatable cuff 184 wherein a rubber bag 185 is employed. The prior cuff 184 is thick as a whole and accordingly is largely corrugated when being wound around the arm 80 in the deflated state thereof. When the cuff 184 is put into the inflated state thereof, an inner member 118 is so deformed as to comply with an inner portion 185 of the rubber bag, and acute grooves 186 are formed in the inner portion 117 as shown in FIG. 9. The acute grooves 186 pinch the skin of the arm 80, thereby producing congestive linear marks in the patient's skin. In contrast thereto, since in the present embodiment the inner space 38 is air-tight, the air located in an outer section 38a of the air-tight space 38 is moved to an inner section 38b of the same 38, when a pressurized air is supplied into the inflatable bag 40. Because of the existence of the air between the inner member 18 and the inflatable bag 40 in the air-tight space 38, the inner member 18 is effectively prevented from being so deformed as to comply with the inner portion 83 of the inflatable bag 40, even if the corrugated cuff 10 wound around the arm 80 is inflated and accordingly acute wrinkles are formed in the inner portion 83 of the bag 40 as shown in the right-hand half of FIG. 7. In addition, since the outer member 16 has an elasticity, the outer member 16 is elongatable in the longitudinal direction of the cuff 10, by an amount greater than that of the inner member 18. Thus, the respective corrugations of the inner member 18 and the inner portion 83 of the inflatable bag 40 due to the respective differences between the diameters of the inner and outer members 18, 16 and between the diameters of the inner and outer portions of the bag 40, are reduced, and the production of acute wrinkles are minimized. Since the inflatable bag 40 is very thin and accordingly the cuff 10 as a whole is thin, the corrugation of the cuff 10 in the deflated state thereof is small. Therefore, acute grooves are not formed in the inner surface 17 of the inner member 18 as shown in the right-hand half of FIG. 7, and thus congestive marks are not produced in the skin of the patient. Even if the cuff 10 is repetitively inflated and deflated for measuring blood pressure values of the patient and thereby monitoring the blood pressure of the patient for a long period of time, the patient is free from the production of congestive marks or other discomforts due to the repetitive use of the cuff 10.

In the case where a blood pressure measurement is effected on an infant having a thin upper arm 80, the cuff 10 may be used by folding the cuff 10 back along the folding-position line 66 provided on the outer surface 15 and securing the cuff-folding fastener pads 70, 72 to the outer surface 15 as shown in FIG. 6. Accurate blood pressure measurements need the use of an inflatable cuff having an appropriate width falling within a predetermined range corresponding to the circumferential length of the upper arm 80 of the patient. Since a conventional cuff such as the cuff 184 shown in FIG. 9 has a great thickness, the conventional cuff cannot be used by folding it back like the cuff 10. In contrast, the cuff 10 as a whole is thin and the inflatable bag 40 is very thin, so that the cuff 10 can easily be folded back. No air is supplied to the folded-back portion (i.e., portion between the line 66 and edge 22) of the bag 40. The cuff 10 can be used commonly for both adults and infants, and thus the cuff 10 can be used widely.

Figure 8A:
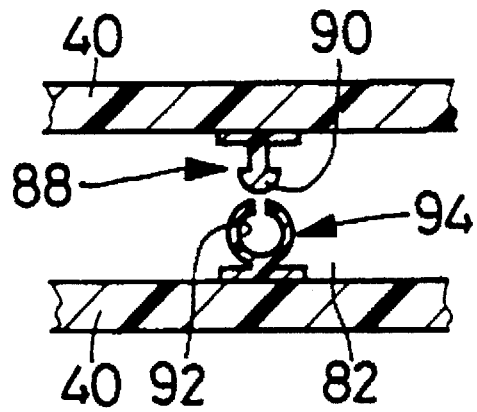
FIG. 8(a) is a cross-sectional view of a width adjustment device employed in a modified form of the cuff of FIG. 1.
Figure 8B:
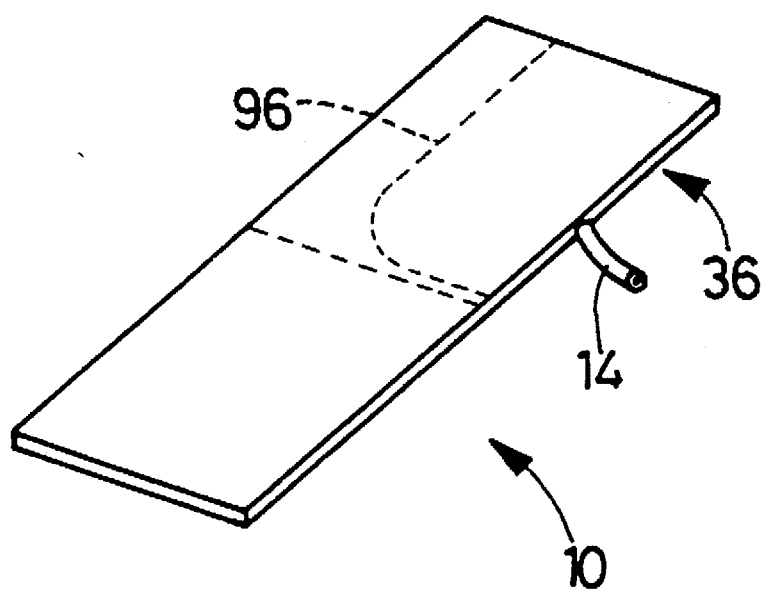
FIG. 8(b) is a perspective view of the modified cuff of FIG. 8(a), showing the position of provision of the width adjustment device in the cuff.

FIGS. 8(a) and 8(b) show a width adjustment device 96 which may be used in place of the folding-position line 66 and cuff-folding fastener pads 70, 72. The width adjusting device 96 is a sealing resin fastener extending from the distal long edge 12 to the first short edge 24 as indicated at a broken line in FIG. 8(b). The resin fastener 96 includes a first engagement member 88 having a thickened top portion 90, and a second engagement member 94 having a grooved top portion 92 with which the thickened top portion 90 can be engaged. The first and second engagement members 88, 94 are provided on opposite inner surfaces of the inflatable bag 40. With the width adjust device 96, the width of the inflatable chamber 82 of the bag 40 can be adjusted to the circumferential length of a body portion of a living subject.

Since in the present embodiment the outer layer 54 of the inner member 18 is formed of a non-woven cloth, a layer of air remains between the skin of the arm 80 and the cuff 10 even when the cuff 10 is inflated around the arm 80. When the cuff 10 is used on the arm 80 for a long period of time, the cuff 10 effectively prevents the skin of the arm 80 from becoming sweaty or sodden, thereby reducing the discomfort of the patient.

In the present embodiment, the outermost layer 52 of the outer member 16 is formed of a nylon pile, and the hooks 68, 74 of the fastener pads 70, 72, 76 are easily held in engagement with the looped fibers of the nylon pile. Therefore, the cuff 10 does not need a fastener having a multiplicity of loops which is usually used in combination with the fastener 70, 72, 76 according to JIS L0213. Thus, the overall thickness of the cuff 10 is reduced.

Since the cuff 10 is produced using the nylon pile, non-woven cloth, polyethylene, and ethylene-vinyl acetate resin, no poisonous gas is produced when the cuff 10 is burnt. Thus, the cuff 10 is advantageously used as a disposable cuff in the case where it is required that different cuffs be used for individual patients. However, the cuff 10 is not limited to the use of a disposable cuff.

While the cuff 10 is adapted to be wound around the upper arm 80, the cuff 10 may be modified to be wound around a different body portion of a living subject. In the latter case, it is possible to change the inclination angles Θ of the cuff-winding graduations 62, or the particular range of measurement graduations 58 for which the cuff-winding graduations 62 are provided, depending upon the body portion where blood pressure measurements are effected.

Although in the present embodiment both of the opposite outer surfaces of the inflatable bag 40 are not fixed to the outer member 16 or the inner member 18 and the air-tight space 38 is defined by the inflatable bag 40 and the outer and inner members 16, 18, it is otherwise possible to provide an air-tight space defined by the inflatable bag 40 and the inner member 18 only. In other words, one of the opposite outer surfaces of the inflatable bag 40 may be fixed to the outer member 16.

While in the present embodiment both the outer and inner members 16, 18 have respective elasticities, it is possible to form the inner member 18 of a material which does not have elasticity.

In the present embodiment, the inflatable bag 40 has an emboss finishing in the outer surfaces thereof, and the bag 40 is easily movable relative to the inner member 18. However, the emboss finishing may be omitted.

Although in the present embodiment the cuff 10 has the original width of 14 cm for use with adults and the adjusted width of 8 to 9 cm for use with infants, it is possible to modify the cuff 10 such that the modified cuff has an original width for use with king-sized persons and an adjusted width for use with adults. By providing a plurality of folding-position lines 66 on the outer surface 15 of the cuff 10, it is possible to adapt the cuff 10 to have an original width for use with king-sized persons, a first adjusted width for use with adults, and a second adjusted width for used with infants.

In the present embodiment, the cuff-folding fastener pads 70, 72 are employed for securely holding the adjusted width of the cuff 10 till the folded cuff 10 is wound around the upper arm 80. However, the fastener pads 70, 72 may be omitted because those are not essentially necessary after the cuff 10 is wound around the arm 80.

Figure 11:
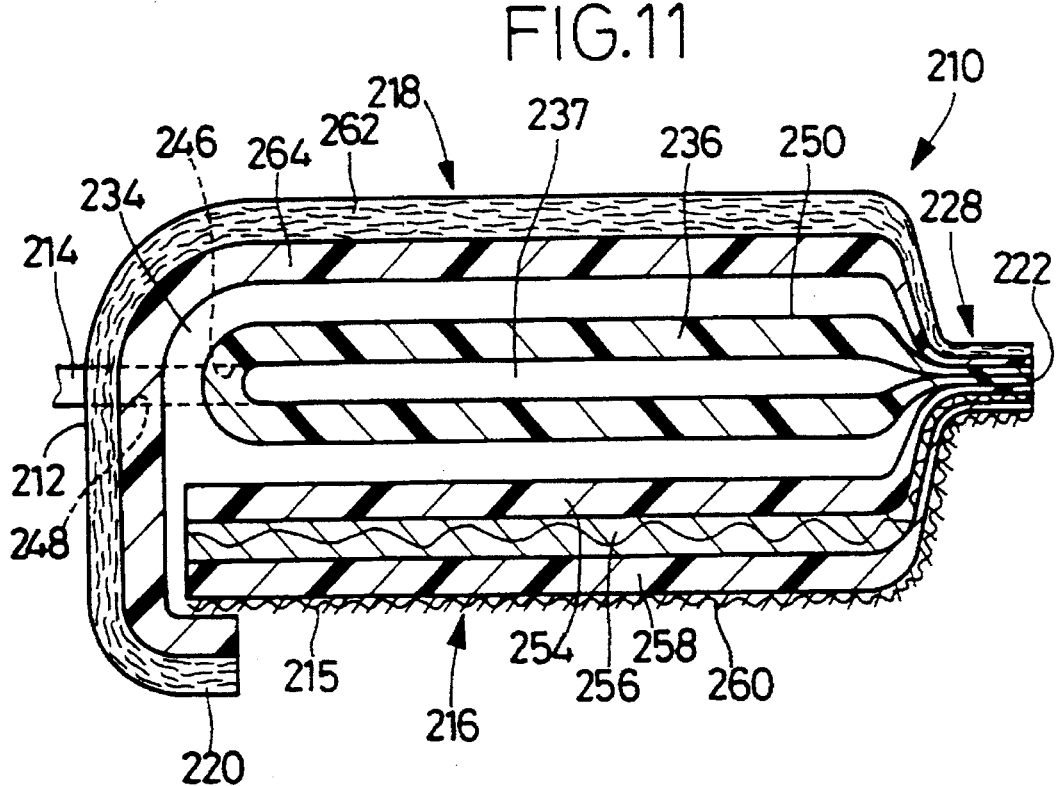
FIG. 11 is an illustrative, transverse cross-sectional view of the cuff of FIG. 10 taken along Line 11—11 of FIG. 10.
Figure 12:
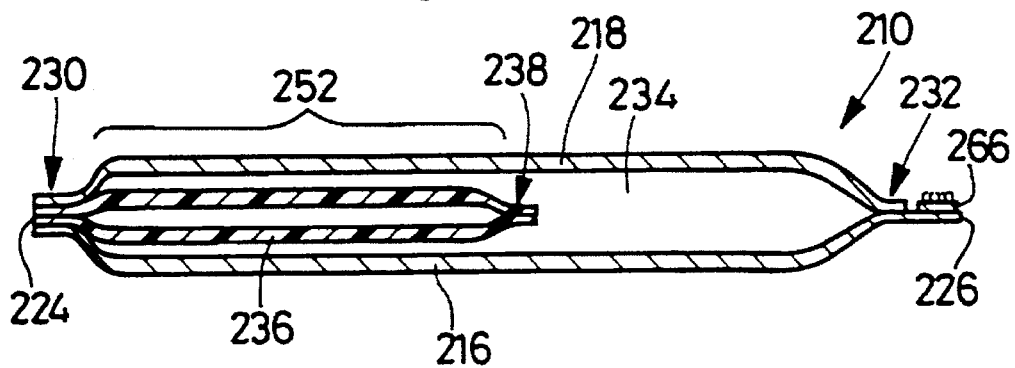
FIG. 12 is an illustrative, longitudinal cross-sectional view of the cuff of FIG. 10 taken along Line 12—12 of FIG. 10.

Referring next to FIGS. 10 to 15, there is shown a second embodiment of the present invention. The second embodiment also relates to an inflatable cuff for being used in measuring a blood pressure of a living subject such as a patient. FIG. 10 shows an inner major surface 217 of the present cuff 210. The inner surface 217 is not externally exposed or visible to a user, and contacts an upper arm 268, with the cuff 210 being wound around the arm 268 (FIG. 15). FIG. 11 shows a transverse cross-sectional view of the cuff 210 taken along Line 11—11 of FIG. 10, and FIG. 12 is a longitudinal cross-sectional view of the cuff 210 taken along Line 12—12 of FIG. 10.

The cuff 210 has an outer major surface 215 having the same structural features as those shown in FIG. 1, i.e., having measurement graduations, cuff-winding graduations, folding-position line, and cuff-folding fastener pads corresponding to the elements 58, 62, 66, 70, 72 of FIG. 1.

The cuff 210 has a belt-like configuration with an about 50 cm length, an about 14 cm width, and an about 1.5 mm thickness. As shown in FIG. 15, an air pipe 214 is connected to a distal long edge 212 of the cuff 210. The distal long edge 212 is more distant from the heart of the subject, than an opposite, proximal long edge 222 of the cuff 210, with the cuff 210 being wound around the arm 268. The cuff 210 is connected via the air pipe 214 to a pressurized-air supplying and discharging device (i.e., air pump 274 and valve device 272 shown in FIG. 15), when the cuff 210 is used in measuring a blood pressure value of the patient.

The cuff 210 includes an outer member 216 defining the outer surface 215, and an inner member 218 defining the inner surface 217. As shown in FIG. 11, the inner member 218 is folded back to provide a folded portion 220 along the distal long edge 212 of the cuff 210. The inner member 218 is adhered to the outer member 216 at the folded portion 220 along the distal long edge 212. In addition, the inner and outer members 218, 216 have a first, a second, and a third sealing portion 228, 230, 232 along the proximal long edge 222 and a first and a second short edge 224, 226, respectively. The inner and outer members 218, 216 are welded to each other by thermocompressing the three sealing portions 228, 230, 232 so that an inner space 234 is defined by the folded portion 220 and the sealing portions 228, 230, 232.

As shown in FIG. 12, an inflatable bag 236 having a length about a half of the lengths, and substantially the same width as the widths, of the inner and outer members 218, 216 is provided in the inner space 234 of the cuff 210. The inflatable bag 236 is formed by folding a resin sheet along the distal long edge 212, subsequently welding by thermocompressing a pair of sealing portions 238 of the sheet, and finally welding by thermocompressing respective open edges thereof corresponding to the sealing portions 228, 230 of the inner and outer members 218, 216 simultaneously with the thermocompressing of the two members 218, 216. The resin sheet used for the bag 236 is, for example, an ethylene-vinyl acetate resin film formed of a composition containing 15 to 20% of vinyl acetate and 85 to 80% of linear low-density polyethylene (LDPE), and having an about 0.02 mm thickness. This resin film possesses a high tensile strength and a high elongation. It is preferred that the inflatable bag 236 be so finished as to have a multiplicity of fine bosses in a major surface 250 thereof which is to contact respective inner layers 264, 254 of the inner and outer members 218, 216.

Figure 13:
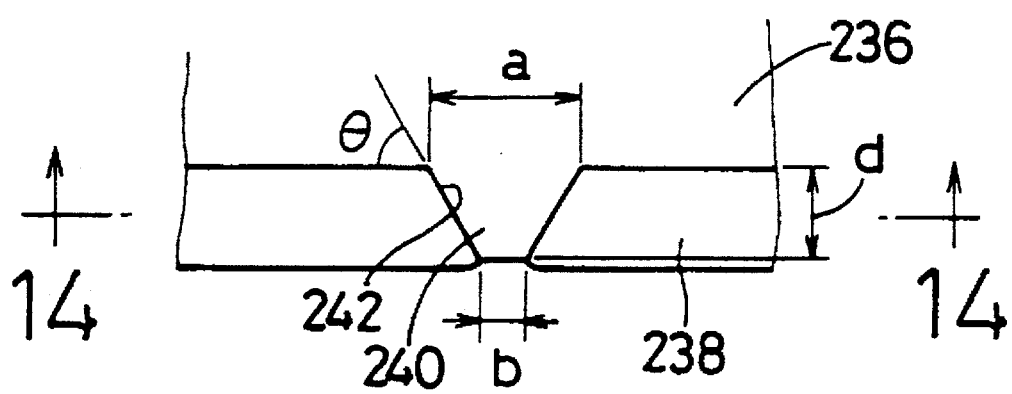
FIG. 13 is an enlarged view of a part of a pair of sealing portions of an inflatable bag of the cuff of FIG. 10.
Figure 14:
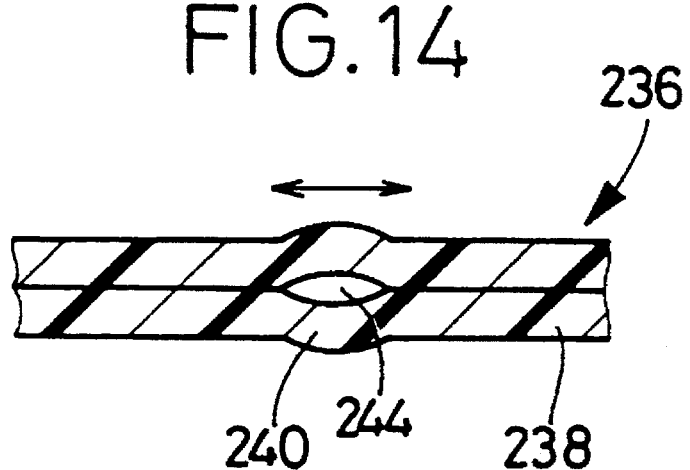
FIG. 14 is a cross-sectional view of the part of the sealing portions of FIG. 13 taken along Line 14—14 of FIG. 13.

FIG. 13 is an enlarged view of an intermediate portion of the sealing portions 238 of the inflatable bag 236. The sealing portion 238 include a pair of non-sealing areas which are not sealed upon welding of the sealing portions 238. The non-sealing areas cooperate with each other to define a relief channel 240 which has, e.g., a dimension, a, of about 2.5 to 3.5 mm, a dimension, b, of about 1.5 to 2.5 mm, and an angle, $\Theta$, of about 60 degrees contained by the longitudinal direction of the sealing portions 238 and a prolongation line of a boundary line 242 between the sealing and non-sealing areas. The sealing portions 238 have, e.g., a width, d, of about 3 mm. When the inflatable bag 236 is inflated, first, the relief channel 240 remains closed because of an elastic force of the resin film of the bag 236 and a tensile force produced in a direction indicated at arrow in FIG. 14 upon inflation of the bag 236. However, when an air pressure in an inflatable chamber 237 of the bag 236 exceeds a predetermined pressure level, the relief channel 240 opens as indicated at 244 in FIG. 14.

The inner member 218 and the inflatable bag 236 have respective through-holes 248, 246 through which the air pipe 214 is inserted to communicate the inflatable chamber 237 in the bag 236 with the air supplying and discharging device 72, 74 of FIG. 5. The air pipe 214 is air-tightly fixed to the inner member 218 and the inflatable bag 236 by thermocompressing. The major surface 250 of the inflatable bag 236 is not entirely fixed, that is, is displaceable relative to the inner and outer members 218, 216, except for the respective edge portions thereof corresponding to the sealing portions 228, 230, and the through-hole 246 that is fixed to the inner member 218 via the air pipe 214. Reference numeral 52 designates a pressing portion as a part of the cuff 210.

The outer member 216 has a four-layer integral structure including (a) an innermost or first layer 254 formed of a polyethylene resin and having an about 0.04 mm thickness; (b) a second layer 256 formed of a cloth woven using fibers of a polyethylene from a medium or low pressure polymerization process, at a weaving density of 10×10/inch; (c) a third layer 258 formed of a polyethylene resin and having an about 0.04 mm thickness; and (d) an outermost or fourth layer 260 formed of a nylon pile produced in a 40/20 yarn usage having a weight of 65 g/m$^2$, and including fibers finely corrugated in the longitudinal direction of the cuff 210 and a multiplicity of looped fibers exposed in the outer surface 215 of the cuff 210. The first and second layers 254, 256 are employed for increasing the tensile strength of the outer member 216, thereby preventing the member 216 from breaking when the bag 236 is inflated and accordingly the member 216 is elongated in the longitudinal direction of the cuff 210. Because of the use of the corrugated fibers in the outermost layer 254 and the use of the polyethylene resin in the third layer 258, the outer member 216 has an elasticity which permits the cuff 210 to be elastically elongatable in the longitudinal direction of the cuff 210.

The inner member 218 has a two-layer integral structure including (a) an outer layer 262 formed of a non-woven cloth which is produced using a 50% rayon, 50% polyester blended yarn and has a weight of 60 g/m² and a thickness of about 0.55 mm; and (b) an inner or lining layer 264 formed of a polyethylene resin and having an about 0.05 mm thickness. Because of the use of the non-woven cloth in the outer layer 262 and the use of the polyethylene resin in the lining layer 264, the inner member 218 has an elasticity in the longitudinal direction of the cuff 210. In FIGS. 10 and 12, reference numeral 266 designates a fastener pad including a multiplicity of hooks. The winding of the cuff 210 around the upper arm 268 is started with an end portion including the first short edge 224, such that the outer member 216 is externally exposed, i.e., does not contact the skin of the arm 268. The winding of the cuff 210 is ended by pressing the fastener pad 266 on the looped fibers of the outer layer 260 of the outer member 216 and thereby holding the hooks of the fastener pad 270 in engagement with the looped fibers of the outer layer 260. Thus, the cuff 210 wound around the arm 268 is fixed to the arm 268 and is ready for use in measuring a blood pressure of the patient. In FIGS. 11 and 12, the respective elements or parts of the cuff 210 are not illustrated with their accurate dimensions relative to each other, but for illustrative purposes only.

The cuff 210 is wound around the upper arm 268 of the patient, as shown in FIG. 15. In the case where blood pressure values of the patient are repeatedly measured, the cuff 210 is used with an automatic blood pressure (BP) monitoring apparatus 270 including the pressurized air supply and discharging device, i.e., air pump 274 and valve device 272. In this case, the air pipe 214 is connected to the valve device 72. The BP monitor apparatus 70 includes a timer, and a control device which automatically operates, according to the contents of the timer, the valve device 72 to supply a pressurized air to, and discharge the air from, the cuff 210 at predetermined intervals of time. The control device of the apparatus 270 determines a systolic and a diastolic BP value of the patient by utilizing Korotkoff sounds detected by a microphone 276 in each measurement cycle, and outputs the determined BP values on a display (not shown) or on a record sheet through a recorder (not shown). The BP value determining method is well known in the art and, hence, the description thereof is omitted.

In the event that the automatic BP monitor apparatus 270 shows a significantly large change in the patient's BP values, a medical worker, such as a doctor or a nurse, attending to the patient usually removes the cuff 210 connected to the monitor 270, from the upper arm 286, and winds another cuff connected to a mercurial manometer, around the arm 286, to personally measure BP values of the patient using a stethoscope. Thus, the medical worker identifies whether the patient has a physical abnormality. In this case, the medical worker often fails to place the BP monitor apparatus 270 in an inoperative state thereof, because he or she is hurrying to directly measure patient' BP values as soon as possible. Therefore, while the medical worker is directly measuring the patient's BP values or taking medical treatments against the patient's abnormality, the timer may count up the predetermined time and accordingly the control device may start to operate the valve device 272 to inflate the inflatable bag 236 of the cuff 210. In this situation, if the inflatable bag 236 did not have the relief channel 240, the bag 236 would continue to inflate beyond the upper limit of its elasticity and eventually break.

However, in the second embodiment, the inflatable bag 236 of the cuff 210 has the relief channel 240 in the sealing portions 238. When a pressurized air is supplied to the inflatable chamber 237 of the bag 236 to start inflation of the chamber 237 and accordingly the two folded portions of the resin film defining the inflatable chamber 237 therein are separated from each other, the two non-sealing areas defining the relief channel 240 are held in pressed contact with each other because of the tensile force produced in the longitudinal direction of the sealing portions 238 and the elastic force of the resin film. Thus, the relief channel 240 remains closed, as described previously, so that the air does not leak from the chamber 237. However, as the air pressure in the inflatable chamber 237 increases with the cuff 210 being removed off the arm 268, the air flows little by little into the relief channel 240, so that the area of contact of the two non-sealing areas decreases as such. When the air pressure in the inflatable chamber 237 exceeds a reference value depending upon the width d of the sealing portion 238, widths a, b of the non-sealing areas, elasticity of the bag 236, etc., the air starts to leak through the relief channel 240, thereby preventing the bag 240 from being inflated any more and accordingly being broken. With the cuff 210 being wound around the upper arm 268, an excessive inflation of the bag 236 is prevented by the outer and inner members 16, 18, and the area of contact of the two non-sealing areas defining the relief channel 240 is not reduced to below a predetermined value, so that the relief channel 240 remains closed and no air leaks from the inflatable chamber 237 of the bag 236. Thus, the provision of the relief channel 240 does not raise any problems with accurate blood pressure measurements using the cuff 210.

In the second embodiment, the inner member 218 is folded back onto the outer member 216, and is adhered at the folded portion 220 to the outer surface 215 of the outer member 216. Thus, an end portion of the cuff 210 including the distal long edge 12 is free from a welded portion like the sealing portion 228. When the cuff 210 is in use on the upper arm 268 as shown in FIG. 15, no welded portion contacts the skin of the arm 268, thereby reducing the discomfort of the patient due to the winding of the cuff 210 around the arm 268. Since the folded portion 220 is positioned on the outer member 216, the folded portion 220 does not contact the skin of the arm 268, thereby ensuring that a blood pressure measurement is effected with much less discomfort of the patient.

Since the cuff 210 is produced using the nylon pile, non-woven cloth, polyethylene, and ethylene-vinyl acetate resin, no poisonous gas is produced upon burning of the cuff 210. Thus, the cuff 210 is advantageously used as a disposable cuff in the case where different cuffs are required to be used for different patients. However, the cuff 210 is not limited to the use of a disposable cuff.

In the second embodiment, the widths a, b and the angle Θ of the relief channel 240 may be changed depending upon the elasticity and strength of the inflatable bag 236, the reference pressure value at which the channel 240 opens, the width d of the sealing portions 238, and etc. For example, the widths a, b may be prescribed as being equal to each other and the angle e equal to 90 degrees.

The width d of the sealing portions 238 of the inflatable bag 236 may be changed depending upon a required resistance of the bag 236 against the pressure produced in the inflatable chamber 237 of the bag 236.

The relief channel 240 may be provided at a position different from the middle of the sealing portions 238, for example, a position near to the proximal or distal long edge 212, 222. However, if the channel 240 is provided too near to the long edge 212, 222, the two non-sealing areas defining the channel 240 may not sufficiently be separated from each other when the bag 240 is inflated with the cuff 210 being not in use off the upper arm 268. Therefore, it is preferable to provide the relief channel 240 around the middle of the sealing portions 238.

The outer surface 250 of the inflatable bag 236 may be fixed to one or both of the outer and inner members 16, 18, except for a portion thereof around the sealing portions 238, i.e., around the central portion of the cuff 210.

One or both of the outer and inner members 16, 18 may not have an elasticity, i.e., may be formed of a material which cannot be elongated in the longitudinal direction of the cuff 210.

While the cuff 210 is adapted to be wound around the upper arm 268, the cuff 210 may be modified to be wound around a different body portion of a living subject.

In the second embodiment, the inflatable bag 236 has emboss finishing in the outer surface 250, and the bag 238 is easily movable relative to the outer and inner members 16, 18. However, the emboss finishing may be omitted.

Referring next to FIGS. 16–22, there are shown a third and a fourth embodiment of the present invention. The third and fourth embodiments also relate to an inflatable cuff for being used in measuring a blood pressure of a living subject such as a patient. The third cuff 310 is employed in an automatic blood pressure measuring apparatus 312 shown in FIG. 21. The fourth cuff 370 (FIG. 20) may be employed in place of the third cuff 310 in the apparatus of FIG. 21.

As shown in FIG. 21, the cuff 310 has a pressing bag 314 connected to a pressure sensor 316, a pressure regulator valve 318, and an air pump 322 via a selector valve 320. The pressure sensor 316 detects an air pressure in the pressing bag 314, and generates a detection signal, SP, representing the detected air pressure. The regulator valve 318 is controllable such that the cross-sectional area of an air passage thereof is changeable to slowly or quickly deflate the pressing bag 314 of the cuff 310. The selector valve 220 is a solenoid-operated valve which is controllable such that the valve. 220 is selectively placed in an air-supplying position and an air-discharging position. In the air-supplying position, the selector valve 220 communicates the pressing bag 314 with an outlet of the air pump 222 and simultaneously communicates an inlet of the air pump 222 with ambient atmosphere. Meanwhile, in the air-discharging position, the selector valve 220 communicates the pressing bag 314 with the inlet of the air pump 222 and communicates the outlet of the air pump 222 with the ambient atmosphere. The air pump 222 produces, at the inlet thereof, a vacuum whose pressure is lower than a pressure of the ambient atmosphere, i.e., atmospheric pressure.

The detection signal SP of the pressure sensor 316 is supplied to a low-pass filter 324 and a band-pass filter 328. The low-pass filter 324 permits only a static-pressure component of the detection signal SP to pass therethrough, thereby providing a cuff-pressure signal, SK, representing the air pressure of the cuff 310. The cuff-pressure signal SK is supplied to a central processing unit (CPU) 330 via an analog to digital (A/D) converter 326. The band-pass filter 328 permits only an oscillation component of the detection signal SP to pass therethrough, thereby providing a pulse wave signal, SM, representing a pressure oscillation produced in the cuff 310 in synchronism with heartbeat of the patient. The pulse wave signal SM is also supplied to the CPU 330 via the A/D converter 326.

The CPU 330 cooperates with a read only memory (ROM) 332, a random access memory (RAM) 334, and an interface 336 to provide an arithmetic control device 337 which serves as blood pressure (BP) determining means described later. The CPU 330 processes input signals according to control programs pre-stored in the ROM 332 by utilizing a temporary-storage function of the RAM 334. The CPU 330 operates an output device 338 to display BP values of the patient on a CRT display (not shown) and/or record the BP values on a record sheet (not shown), on one hand, and operates the regulator valve 318, selector valve 320, and air pump 322, on the other hand.

The CPU 330 receives a first START signal, MS, from a START switch 340, and a STOP signal, MT, from a STOP switch 342. The CPU 330 also receives a second START signal, CS, from a START signal generator 344. A MANUAL/AUTO selector switch 346 is operable for selectively connecting one of the START switch 340 and the START signal generator 344 to the CPU 330. The START signal generator 344 includes, for example, a well-known flip-flop circuit (not shown) and repetitively generates a second START signal CS at a period pre-set through a period-setting device (not shown).

Figure 16:
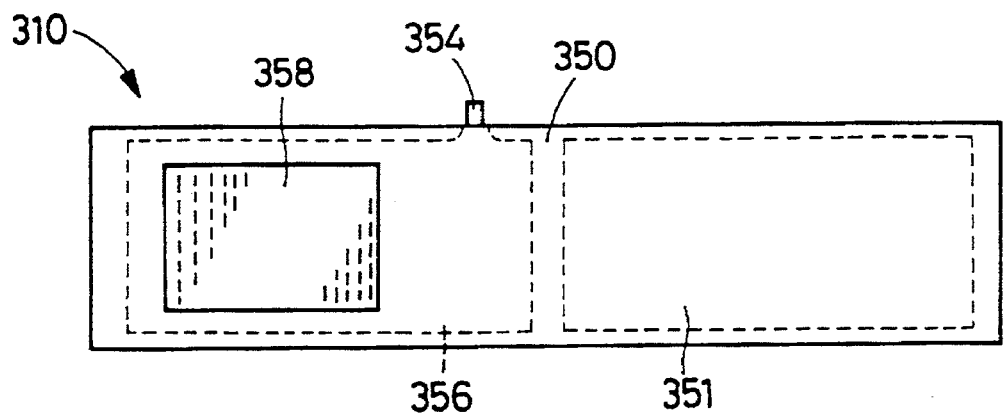
FIG. 16 is a plan view of an outer surface of another inflatable cuff as a third embodiment of the present invention.
Figure 17:
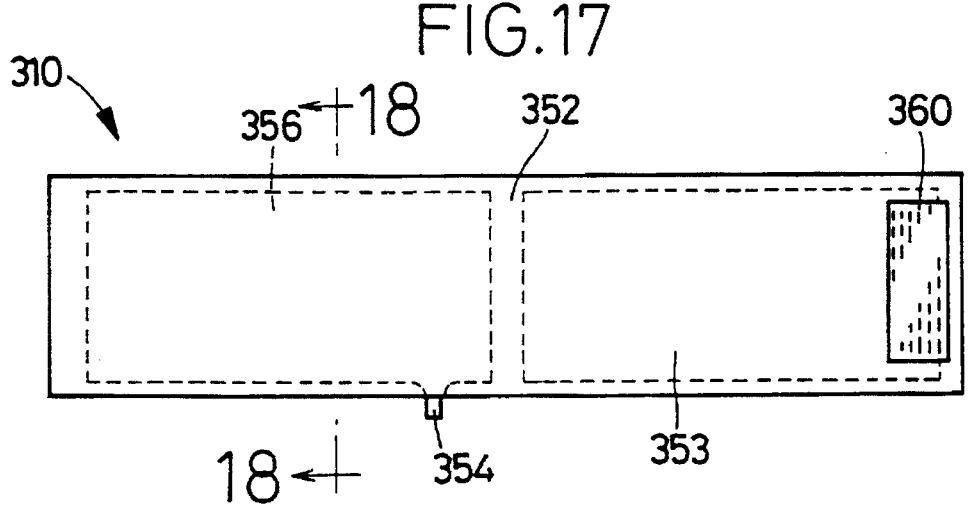
FIG. 17 is a plan view of an inner surface of the cuff of FIG. 16.
Figure 18:
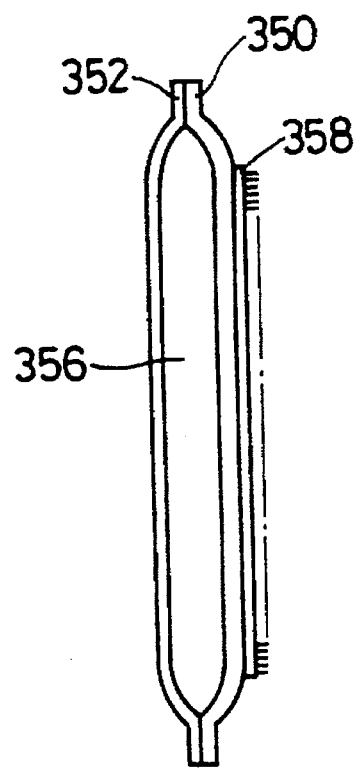
FIG. 18 is a transverse cross-sectional view of the cuff of FIG. 16 taken along Line 18—18 of FIG. 17.

FIG. 16 shows an outer major surface 351 of the cuff 310, FIG. 17 shows an inner major surface 353 of the cuff 310, and FIG. 18 shows a cross-section of the cuff 310 taken along Line 18—18 of FIG. 16. As shown in FIGS. 16–18, the cuff 310 includes an outer member 350 and an inner member 352. The outer member 350 has a belt-like shape and is formed of an elastic sheet such as a synthetic-resin sheet (e.g., soft vinyl-chloride sheet or nylon sheet). The inner member 352 has the same shape as that of the outer member 350 and is bonded with an adhesive or by high-frequency welding to the outer member 350 at sealing portions (indicated in broken lines) provided along the outer periphery of the outer and inner members 350, 352 and at a central location in the longitudinal direction of the members 350, 352 or cuff 310. Thus, the cuff 310 has an air-tight inflatable chamber 356 which extends about half the longitudinal length of the cuff 310. The air-tight chamber 356 is connected via an air pipe 354 to the automatic BP measuring apparatus 312.

A first fastener pad 358 is sewn to the outer surface 351 of the cuff 310, while a second fastener pad 360 is sewn to the inner surface 353 of the cuff 310. When the cuff 310 is wound around, for example, an upper arm (not shown) of the patient, the two fastener pads 358, 360 are disengageably held in engagement with each other. One of the two pads 358, 360 has a multiplicity of hooks formed of a synthetic resin, and the other pad has a multiplicity of looped fibers to be engaged with the hooks of the first fastener pad.

Alternatively, the outer member 350 of the cuff 310 may be modified to have the same structural features as those shown in FIG. 1, i.e., have measurement graduations, cuff-winding graduations, folding-position line, and cuff-folding fastener pads corresponding to the elements 58, 62, 66, 70, 72 of FIG. 1.

Figure 19:
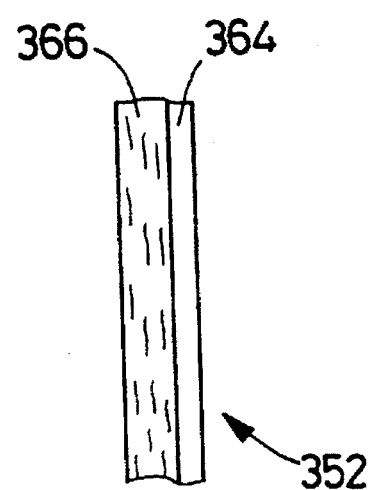
FIG. 19 is an enlarged cross-sectional view of a part of an inner sheet member of the cuff of FIG. 16.

As shown in FIG. 19, the inner member 352 includes a first layer 366 formed of a multiplicity of fibers and a second layer 364 lining an inner surface of the first layer 366. The second layer 364 is formed of a resin film having, e.g., 50 to 100 μm. The resin used may be a synthetic resin selected from nylon, polyethylene, polypropylene, and polyolefine. The first layer 366 may be a nylon-based or polyolefine-based non-woven cloth having a weight of about 20 to 50 g/m$^2$. The second layer 364 prevents air from leaking from the air-tight chamber 356 through the fibrous layer 366 of the cuff 310.

Since the fibrous layer 366 of the inner member 352 is adapted to contact the skin of the upper arm of the patient when the cuff 310 is wound around the arm, air is permitted to flow through fine spaces between the fibers of the fibrous layer 336, so that the skin is kept dry and prevented from become sweaty or sodden.

Since the inner surface 353 of the cuff 310 is not provided with a flexible bag having a number of air holes through which air is flowed out, the cuff 310 can be wound around the upper arm of the patient with a substantially uniform pressing force over the entire circumferential length of the arm. Thus, the accuracy of blood pressure measurements is not reduced.

Figure 20:
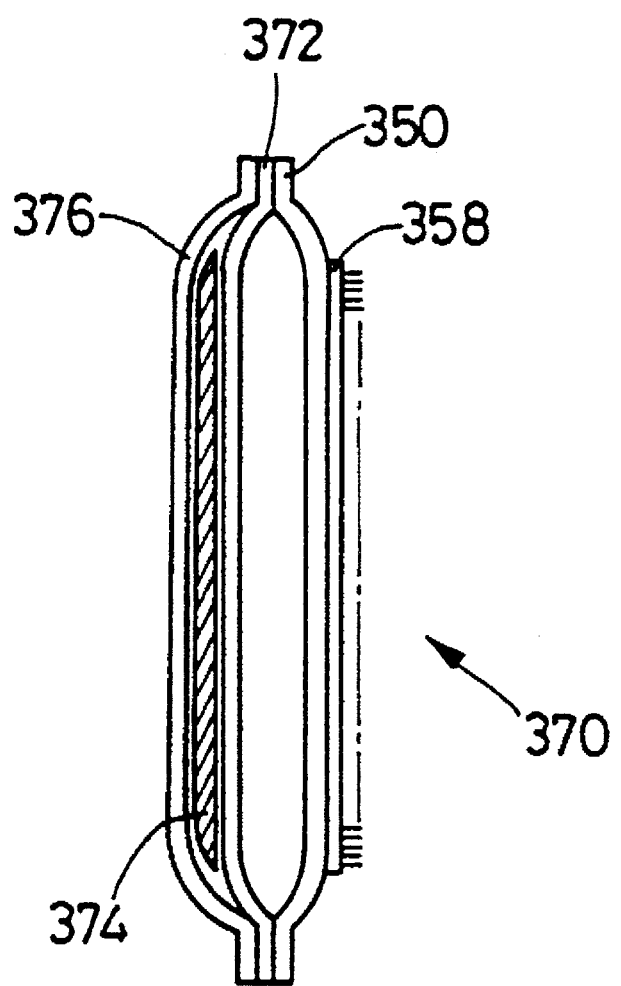
FIG. 20 is a transverse cross-sectional view corresponding to FIG. 18, showing another inflatable cuff as a fourth embodiment of the present invention.

FIG. 20 shows a cross-sectional view of the fourth cuff 370. The cuff 370 includes the same outer member as the element 350 of the cuff 310 of FIG. 16, and an inner member 372 different from the element 352 of the cuff 310. However, the outer member 350 of the fourth cuff 370 may be modified to have the same structural features as those shown in FIG. 1, i.e., have measurement graduations, cuff-winding graduations, cuff-folding line, and cuff-folding fastener pads corresponding to the elements 58, 62, 66, 70, 72 of FIG. 1. A water-absorbing resin sheet 374 and a porous sheet 376 are superposed on the inner member 372, and the outer and inner members 350, 372 and the porous sheet 376 are bonded to one other with an adhesive or by high-frequency welding like the cuff 310. Thus, the resin sheet 374 is supported by the porous sheet 376. The inner member 372 may be a sheet formed of a soft synthetic resin such as vinyl chloride, nylon, polyethylene, polypropylene, or polyolefine. The inner and outer members 350, 372 cooperate with each other to define an air-tight inflatable chamber 356.

The water-absorbing resin sheet 374 includes a nonwoven cloth, and a water-absorbing resin lining the nonwoven cloth. The water-absorbing resin used may be a crosslinking-contained, hydrophilic high-molecular compound. The water-absorbing resin may be obtained by reacting, with a known cross-linking agent, a hydrophilic high-molecular compound such as an anionic derivative of cellulose, starch-polyacrylamide, polyvinylpyrrolidone, polymer of maleic acid, or polymer of acrylic acid. The resin sheet 374 absorbs moisture or water (e.g., sweat) coming out from the skin of the patient. The resin sheet used is capable of absorbing several hundred times as much water as the volume thereof, and finally changes into a gel. The porous sheet 376 is formed of a thin resin sheet having a multiplicity of fine slits which permits the patient's moisture to pass therethrough and diffuse toward the water-absorbing resin sheet 374.

Since the water-absorbing resin sheet 374 and the porous sheet 376 are superposed on the inner member 372 of the cuff 370, the moisture coming out from the patient's skin in contact with the inner member 372 passes through the porous sheet 376 and is absorbed by the water-absorbing resin sheet 374. Thus, the patient's skin is effectively prevented from becoming sweaty or sodden.

Since, like the inner member 352 of the cuff 310 of FIG. 16, the inner member 372 of the fourth cuff 370 is not provided with a flexible bag having a number of air holes through which air is flowed out, the cuff 370 can be wound around the upper arm of the patient with a substantially uniform pressing force over the entire circumferential length of the arm. The accuracy of blood pressure measurements using the cuff 370 is kept high.

Figure 22:
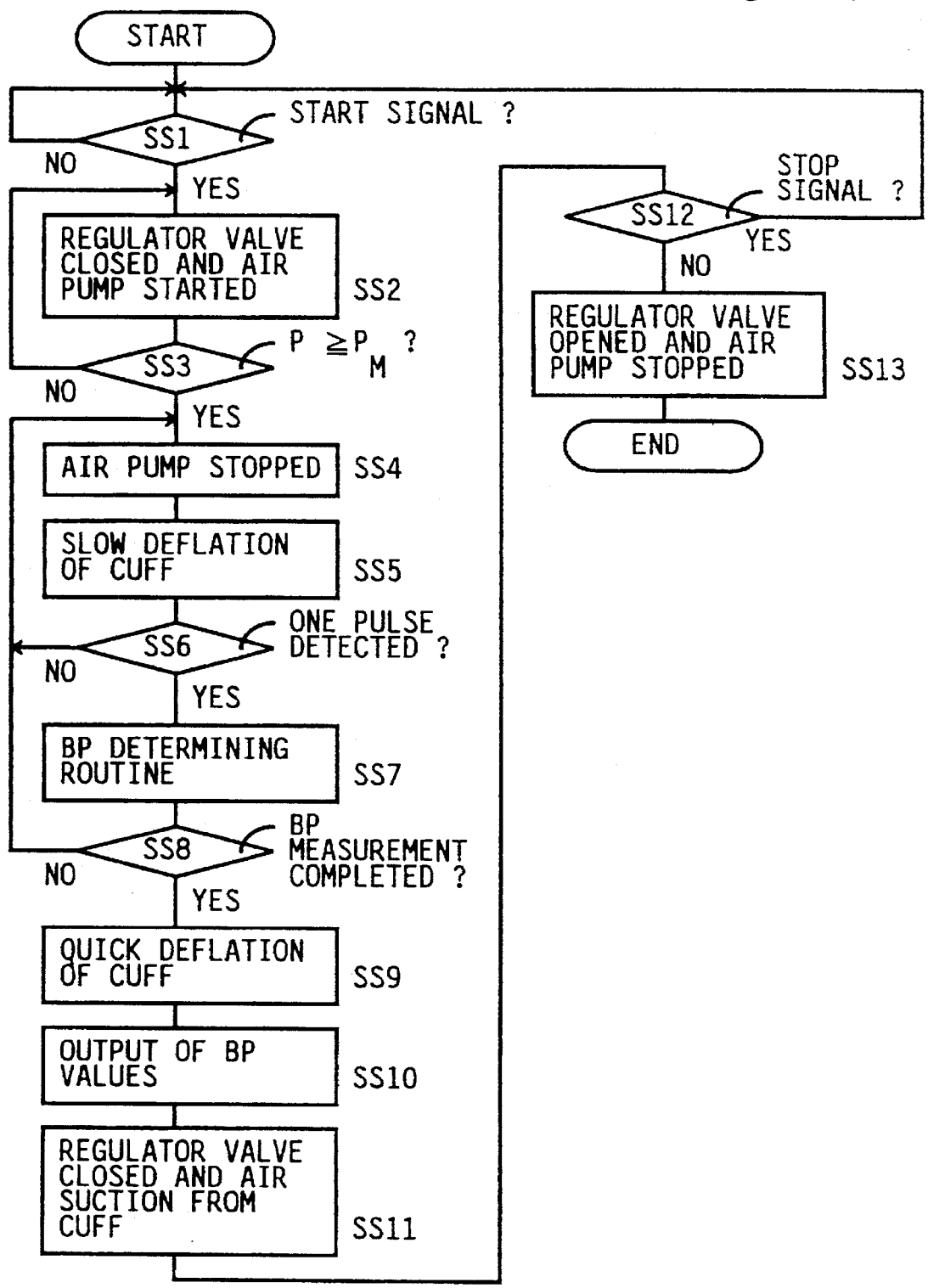
FIG. 22 is a flow chart representing a control program according to which the apparatus of FIG. 21 operates.

FIG. 22 shows a flow chart representing a control program according to which the automatic BP measuring apparatus 312 of FIG. 21 operates.

First, at Step SS1, the CPU 330 judges whether the first or second START signal MS, CS is present at the CPU 330. If a negative judgment is made at Step SS1, the CPU 330 repeats this step. Meanwhile, if a positive judgment is made, the control of the CPU 330 proceeds with Step SS2 to close the pressure regulator valve 318, place the selector valve 220 in the air-supplying position, and operate the air pump 222 so as to start inflation of the cuff 310, 370, i.e., start increasing an air pressure, P, of the cuff 310, 370. Step SS2 is followed by Step SS3 to judge whether the cuff pressure P has reached a predetermined reference value, $P_M$. If a negative judgment is made at Step SS3, the CPU 330 repeats Steps SS2 and SS3. Meanwhile, if a positive judgment is made at Step SS3, the control of the CPU 330 proceeds with Step SS4 to stop the air pump 322 and subsequently to Step SS5 to partially open the regulator valve 218 and thereby start slow deflation of the cuff 310, 370, i.e., start decreasing the cuff pressure P at a predetermined rate, e.g., about 2 to 3 mmHg/sec.

Step SS5 is followed by Step SS6 to judge whether the CPU 330 has received a length of the pulse wave signal SM corresponding to one heartbeat of the patient (hereinafter, referred to as the one-pulse signal), from the pressure sensor 316. If a negative judgment is made at Step SS6, the CPU 330 repeats Steps SS4 to SS6. Meanwhile, if a positive judgment is made at Step SS6, the control of the CPU 330 goes to Step SS7, that is, BP value determining routine. In this routine, first, the CPU 330 determines an amplitude of the one-pulse signal obtained at Step SS6, by subtracting a lower-peak magnitude of the one-pulse signal from an upper-peak magnitude of the same. When the cuff pressure P is slowly decreased, the respective pulse amplitudes of the pulse wave signal SM first increase and then decrease. The CPU 330 determines a cuff pressure P when the respective pulse amplitudes of the pulse wave signal SM have significantly largely increased, as a systolic blood pressure of the patient; determines a cuff pressure P when the pulse amplitudes have become maximum, as a mean blood pressure of the patient; and determines a cuff pressure P when the pulse amplitudes have significantly largely decreased, as a diastolic blood pressure of the patient. At the following Step SS8, the CPU 330 judges whether the blood pressure measurement at Step SS7 has been completed.

If a negative judgment is made at Step SS8, the CPU 330 repeats Steps-SS4 to SS8. Meanwhile, if a positive judgment is made at Step SS8, the control of the CPU 330 goes to Step SS9 to fully open the regulator valve 318 and thereby quickly deflate the cuff 310, 370 in a predetermined period of time. Step SS9 is followed by Step SS10 to operate the display device 338 to indicate the measured BP values. Subsequently, at Step SS11, the CPU 330 closes the regulator valve 318, places the selector valve 320 in the air-discharging place, and operates the air pump 322 for a predetermined period of time. Thus, the air remaining in the air-tight chamber 356 of the cuff 310, 370 is forcedly discharged therefrom to produce a vacuum in the chamber 356. Step SS11 is followed by Step SS12 to judge whether the STOP signal MT is present at the CPU 330. If a negative judgment is made at Step SS12, the CPU 330 repeats Steps SS1 to SS12. Meanwhile, if a positive judgment is made at Step SS12, the control of the CPU 330 goes to Step SS13 to stop the air pump 322 and open the regulator valve 318. Thus, the current control cycle of the CPU 330 is ended.

It emerges from the foregoing description that the automatic BP measuring apparatus 312 carries out Step SS11 to produce a vacuum in the air-tight chamber 356 during a non-BP measurement period following a BP measurement period carried out in response to a manual operation of the START switch 340 or a periodic generation of a START signal from the signal generator 344. Consequently, the air is discharged from the air-tight chamber 356, and the cuff 310, 370 is deflated, i.e., the thickness of the cuff is reduced. Thus, the area of contact of the cuff 310, 370 with the skin of the patient's arm around which the cuff is wound, is minimized, so that air is permitted to more easily flow between the cuff and the patient's skin, thereby preventing the skin from becoming sweaty or sodden.

While in the third or fourth embodiment the inner member 352, 372 has the same size as that of the outer member 350, the size of the inner member 352, 372 may be reduced to the size of the pressing bag 314.

Although in the third or fourth embodiment the entire inner portion of the pressing bag 314 is provided by the inner member 352, 372, only a part of the inner portion of the pressing bag 314 may be provided by the material of the inner member 352, 372.

While in the third embodiment the fibrous layer 366 of the inner member 352 is formed of a non-woven cloth produced using a multiplicity of synthetic fibers, the fibrous layer 366 may be formed of a woven cloth produced using a multiplicity of synthetic fibers or a non-woven or woven cloth produced using a multiplicity of natural fibers such as cotton fibers or wool fibers.

In the fourth embodiment, the porous sheet 376 may be used in plurality, that is, a plurality of porous layers 376 may be provided on the water-absorbing resin sheet 374. Additionally, a different sort of porous sheet may be provided between the inner member 372 and the resin sheet 374, or between the porous sheet 376 and the resin sheet 374.

The inner member 372 of the fourth cuff 370 may be replaced by the inner member 352 of the third cuff 310.

In the case where the air pump 322 is, for example, a rotary-type positive displacement pump disclosed in Unexamined Japanese Patent Application laid open under Publication No. 63-145636, Step SS11 of FIG. 22 may be modified such that the CPU 330 operates for producing a vacuum in the pressing bag 314 (i.e., air-tight chamber 356) by rotating the pump in the reverse direction opposite to the normal direction to supply the air into the bag 314. In the latter case, the selector valve 320 may be omitted.

Figure 23:
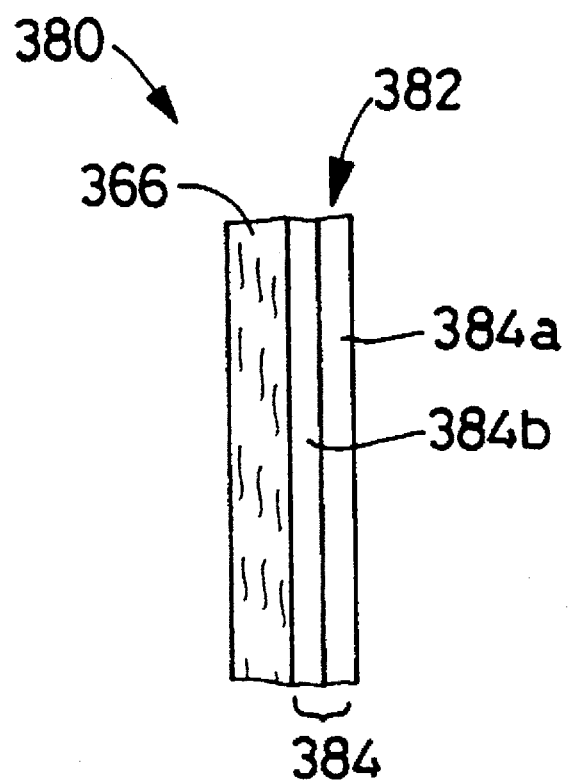
FIG. 23 is an enlarged cross-sectional view corresponding to FIG. 19, showing a part of an inner sheet member of another inflatable cuff as a fifth embodiment of the present invention.

Referring next to FIG. 23, there is shown a fifth embodiment of the present invention. The fifth embodiment also relates to an inflatable cuff for being used in measuring a blood pressure of a living subject such as a patient. The fifth cuff 380 has almost the same structural features as those of the third cuff 310 shown in FIGS. 16 through 19, but is different from the third cuff 310 in that the fifth cuff 380 has an inner member 382 including, in addition to the same fibrous layer 366 as the element 366 of the inner member 352 of the third cuff 310, a porous resin layer 384 different from the resin layer 364 of the inner member 352 of the third cuff 310. The same outer member 350 of the fifth cuff 380 as the element 350 of the third cuff 310 may be modified to have the same structural features as those shown in FIG. 1, i.e., have measurement graduations, cuff-winding graduations, folding-position line, and cuff-folding fastener pads corresponding to the elements 58, 62, 66, 70, 72 of FIG. 1.

The porous resin layer 384 has a multiplicity of pores having a diameter of about 1 to 10 μm, thereby permitting a small amount of air to flow therethrough from an inflatable chamber 356 into the fibrous layer 366. The fibrous layer 366 is securely fixed to the porous resin layer 384, and provides a surface to contact the skin of the patient's upper arm. The density and diameter of the pores of the porous resin layer 384 are pre-determined such that the amount of flow of air therethrough does not adversely affect the accuracy of blood pressure measurement carried out while the air pressure in the inflatable chamber 356 (i.e., pressing force of the cuff 380 applied to the patient's arm) is changed. The porous resin layer 384 has a thickness of, e.g., about 50 to 100 μm. In the present embodiment, the porous layer 384 includes a polyethylene (PE) porous film 384a and an additional porous layer 384b. The porous layer 384 is formed of a porous sheet (e.g., Product No. BRN 1100-C40A) available from Toyo Eizai K.K., Japan. As described previously, the fibrous layer 366 may be formed of a nylon-based or polyolefine-based non-woven cloth having a weight of 20 to 50 g/m$^2$.

The cuff 380 may be employed, in place of the cuff 310, 370, in the automatic BP measuring apparatus 312 of FIG. 21. In this case, too, the apparatus 312 operates according to the flow chart of FIG. 22. The CPU 330 starts operating the air pump 322 and continues the operation for a predetermined time, at Step SS11, in the case where the apparatus 312 is used with the third or fourth cuff 310, 370. However, in the case where the apparatus 312 is used with the fifth cuff 380, the CPU 330 only starts operating the air pump 322 at Step SS11. This operation of the air pump 322 is stopped at Step SS13 in the current control cycle, or at Step SS2 in the next control cycle.

In the fifth embodiment, the inner member 382 of the cuff 380 includes the porous resin layer 384 which permits air to slightly flow from the inflatable chamber 356 therethrough into the fibrous layer 366 adapted to contact the skin of the patient's arm, while a pressing bag 314 is inflated. Therefore, the air flows through fine spaces between the fibers of the fibrous layer 366, although the fibrous layer 366 is held in contact with the patient's skin. Thus, the patient's skin is kept dry and prevented from becoming sweaty or sodden.

Since, like the inner member 352 of the third cuff 310 or the inner member 372 of the fourth cuff 370, the inner member 382 of the fifth cuff 380 is not provided with a flexible bag having a number of air holes from which air is flowed out, the cuff 380 can be wound around the patient's arm with a substantially uniform pressing force over the entire circumferential length of the arm. Thus, the accuracy of blood pressure measurements using the cuff 380 is high.

When the fifth cuff 380 is used with the automatic BP measuring apparatus 312 of FIG. 21, the CPU 330 carries out Step SS11 to produce a vacuum in the inflatable chamber 356 during a non-BP measurement period following a BP measurement period carried out in response to a manual operation of the START switch 340 or a periodic generation of a START signal from the signal generator 344. Consequently, the air is discharged from the inflatable Chamber 356 of the pressing bag 314, and the cuff 380 is deflated, i.e., the thickness of the cuff 380 is reduced. Thus, the area of contact of the cuff 380 with the skin of the patient's arm around which the cuff 380 is wound, is minimized, so that air is permitted to more easily flow between the cuff 380 and the patient's skin, thereby preventing the skin from becoming sweaty or sodden. Furthermore, during the non-BP measurement period, ambient air is sucked into the pressing bag 314 through the fine spaces between the fibers of the fibrous layer 366 because a vacuum is produced in the inflatable chamber 356 of the pressing bag 314 by the air pump 322. Thus, the patient's skin in contact with the pressing bag 314 is more effectively prevented from becoming sweaty.

In the fifth embodiment, the inner member 382 has the same size as that of the outer member 350 of the cuff 380. However, the size of the inner member 382 may be reduced to the size of the pressing bag 314.

Although in the fifth embodiment the entire inner portion of the pressing bag 314 is provided by the inner member 382, only a part of the inner portion of the pressing bag 314 may be provided by the material of the inner member 382.

In the fifth embodiment, the inner member 382 of the cuff 380 has a two-layer integral structure including the porous resin layer 384 and the fibrous layer 366. However, the two layers 384, 366 of the inner member 382 may be provided separably from each other, for example, may be superposed on each other.

In the fifth embodiment, a flexible spacer having a number of straight ridges and grooves, or having corrugation may be provided in the pressing bag 314, so that air is permitted to more easily flow through the cuff 380 when the pressing bag 314 is put in vacuum by the air pump 322.

While the present invention has been described in its preferred embodiments, the invention may otherwise be embodied.

For example, the first cuff 10 or the second cuff 210 may be used, in place of the third or fourth cuff 310, 370, in the automatic BP measuring apparatus of FIG. 21.

It is to be understood that the present invention may be embodied with other changes, improvements, and modifications that may occur to those skilled in the art without departing from the spirit and scope of the invention defined in the appended claims.

What is claimed is:

1. An inflatable cuff for pressing a body portion of a living subject by being wound and inflated around the body portion, in measuring a blood pressure of the subject, the cuff having an elongate rectangular shape having a pair of opposite long edges and a pair of opposite short edges, and comprising:

a first group of graduations provided on a major surface of the cuff, said major surface being adapted to be visible when the cuff is wound around said body portion of said subject, so that said first group of graduations are used for measuring a circumferential length of the body portion; and a second group of graduations provided on said major surface of the cuff, the graduations of said second group corresponding to the graduations of said first group, respectively, so that when the cuff is wound around said body portion of said subject, the cuff is fixed at one of the graduations of said second group which corresponds to one of the graduations of said first group which indicates the circumferential length of the body portion measured by using said first group of graduations, said first group of graduations comprising a plurality of first straight segments which are provided equidistantly from each other along one of said two long edges of the cuff and each of which is perpendicular to said one long edge, said one long edge being adapted to be positioned nearer to a heart of said subject than the other long edge when the cuff is wound around said body portion of the subject, said second group of graduations comprising a plurality of second straight segments which are provided in an intermediate portion of the cuff, each of said straight segments being slightly inclined with respect to a direction parallel to the short edges of the cuff, respective inclination angles of said second straight segments being different from each other, each of said second straight segments being associated with a corresponding one of said first straight segments such that a prolongation line of said each second straight segments intersects, on said one long edge of the cuff, a prolongation line of said corresponding one first straight segment, the circumferential length of the body portion being indicated by one of said first straight segments which is aligned with one of said two short edges of the cuff being cylindrically wound around the body portion, the cuff being fixed around the body portion of the subject by aligning said one short edge with one of said second straight segments which is associated with said one first straight segment indicating the circumferential length of the body portion.

2. An inflatable cuff according to claim 1, further comprising:

a pressing bag having a fluid-tight space therein; and an inflatable bag having an inflatable chamber therein, said inflatable bag being provided in said fluid-tight space of said pressing bag such that a fluid is left outside said inflatable bag and inside said pressing bag, said pressing bag having said major surface of the cuff.

3. An inflatable cuff according to claim 2, wherein said pressing bag comprises:

an inner sheet member adapted to contact said body portion of said subject when the cuff is wound around the body portion; and an outer sheet member which cooperates with said inner sheet member to provide the pressing bag, said fluid comprising an air, at least a portion of said air moving from a first section defined between said outer sheet member and said inflatable bag into a second section defined between said inner sheet member and the inflatable bag when the inflatable bag is inflated with the cuff being wound around the body portion.

4. An inflatable cuff according to claim 1, further comprising:

an inner portion which is adapted to contact said body portion of said subject when the cuff is wound around the body portion; and an outer portion which cooperates with said inner portion to provide a pressing bag adapted to press said body portion of said subject, said outer portion being formed of a material having an elasticity such that the outer portion is elastically deformable up to a prescribed maximum amount when the cuff is inflated around the body portion, said outer portion having said major surface of the cuff.

5. An inflatable cuff according to claim 4, wherein said outer portion is formed of said material comprising at least one of a first layer formed of a multiplicity of corrugated fibers extending in a longitudinal direction of the cuff and a second layer formed of a resin.

6. An inflatable cuff according to claim 1, further comprising:

a pressing bag having said major surface of the cuff and an inner space therein;

an inflatable bag having an inflatable chamber therein, said inflatable bag being provided in said inner space of said pressing bag; and a width adjustment device for adjusting a width of said inflatable chamber in a direction parallel to a center line of the cuff cylindrically wound around said body portion of said subject.

7. An inflatable cuff according to claim 6, wherein said width adjustment device comprises at least one of at least one reference line which is provided parallel to said long edges and along which the cuff is foldable to reduce said width of said inflatable chamber, at least one pair of fastener pads which are provided on said major surface of the cuff and are engageable with each other to fold the cuff, and a sealing device which is provided in said inflatable chamber and includes a first and a second sealing member engageable with each other to reduce said width of the inflatable chamber.

8. An inflatable cuff according to claim 1, further comprising:
a pressing bag having said major surface of the cuff and an inner space therein;
an inflatable bag having an inflatable chamber therein, said inflatable bag being provided in said inner space of said pressing bag, and being formed of an elastic sheet, said inflatable chamber being defined by fluid-tightly sealing a pair of sealing portions of said elastic sheet to each other, said pair of sealing portions having a predetermined width along an outer periphery of said elastic sheet, and including a pair of non-sealing areas which cooperate with each other to define a relief channel which, when the cuff is not in use off said body portion of said subject, does not open before a fluid pressure in said inflatable chamber exceeds a reference value and opens when said fluid pressure of said inflatable chamber exceeds said reference value.

9. An inflatable cuff according to claim 8, wherein said relief channel has an inner width measured on an inner boundary line of said sealing portions having said predetermined width along said outer periphery of said elastic sheet, and an outer width measured on an outer boundary line of said sealing portions, said outer width being smaller than said inner width, so that an area of contact of said pair of non-sealing areas defining the relief channel decreases as an air pressure in said inflatable chamber increases and that the relief channel opens when said air pressure increases up to said reference value and accordingly said area of contact of said non-sealing areas decreases down to a lower limit value.

10. An inflatable cuff according to claim 8, wherein said elastic sheet comprises a resin sheet, said inflatable bag being formed by air-tightly welding a pair of welding portions of said resin sheet as said pair of sealing portions of said elastic sheet.

11. An inflatable cuff according to claim 8, further comprising a pressing bag having an inner space therein, said inflatable bag being provided in said inner space of said pressing bag.

12. An inflatable cuff according to claim 1, further comprising:
an outer sheet member; and
an inner sheet member which cooperates with said outer sheet member to provide a pressing bag adapted to press said body portion of said subject, at least a portion of said inner sheet member including
a first layer formed of a multiplicity of fibers, said first layer having a first surface adapted to directly contact said body portion of said subject when the cuff is wound around the body portion, and
a second layer formed of a resin film, said second layer being fixed to a second surface of said first layer to prevent a fluid from leaking from said pressing bag through the first layer, said second surface being opposite to said first surface,
said outer sheet member having said major surface of the cuff.

13. An inflatable cuff according to claim 12, wherein said fibers used for forming said first layer of said inner sheet member is selected from the group consisting of synthetic fibers such as nylon fibers and polyolefine fibers, and natural fibers such as cotton fibers and wool fibers.

14. An inflatable cuff according to claim 12, wherein said first layer of said inner sheet member is formed of, as said fibers, a cloth selected from the group consisting of a non-woven cloth and a woven cloth.

15. An inflatable cuff according to claim 14, wherein said resin film used for forming said second layer of said inner sheet member is selected from the group consisting of nylon film, polyethylene film, polypropylene film, and polyolefine film.

16. An inflatable cuff according to claim 12, wherein said resin film used for forming said second layer of said inner sheet member has a thickness of 50 to 100 µm.

17. An inflatable cuff according to claim 1, further comprising:
an outer sheet member; and
an inner sheet member which cooperates with said outer sheet member to provide a pressing bag adapted to press said body portion of said subject, at least a portion of said inner sheet member including
a first layer formed of a porous resin film which permits an air to slightly flow from said pressing bag therethrough, and
a second layer formed of a multiplicity of fibers, and provided on said first layer, said second layer being adapted to directly contact said body portion of said subject when the cuff is wound around the body portion,
said outer sheet member having said major surface of the cuff.

18. An inflatable cuff according to claim 17, wherein said porous resin film used for forming said first layer of said inner sheet member has a multiplicity of pores having a diameter of 1 to 10 µm.

19. An inflatable cuff according to claim 17, wherein said porous resin film used for forming said first layer of said inner sheet member comprises a polyethylene film.

20. An inflatable cuff according to claim 17, wherein said porous resin film used for forming said first layer of said inner sheet member has a thickness of 50 to 100 µm.

21. An inflatable cuff according to claim 17, wherein said fibers used for forming said second layer of said inner sheet member are selected from the group consisting of synthetic fibers and natural fibers.

22. An inflatable cuff according to claim 17, wherein said second layer of said inner sheet member is formed of, as said fibers, a cloth selected from the group consisting of a non-woven cloth and a woven cloth.

23. An inflatable cuff according to claim 17, wherein said fibers used for forming said second layer of said inner sheet member are selected from the group consisting of nylon fibers, polyolefine fibers, cotton fibers, and wool fibers.

24. An inflatable cuff according to claim 1, further comprising:
an outer sheet member;
an inner sheet member which cooperates with said outer sheet member to provide a pressing bag adapted to press said body portion of said subject;
a resin sheet which is formed of a resin which absorbs a water, and provided on said inner sheet member; and a porous sheet which is formed of a porous material, provided on said resin sheet, and fixed to said inner sheet member to support said resin sheet, said porous sheet being adapted to directly contact said body portion of said subject when the cuff is wound around the body portion, said outer sheet member having said major surface of the cuff.

25. An inflatable cuff according to claim 24, wherein said resin used for forming said resin sheet is obtained by reacting, with a crosslinking agent, a hydrophilic high-molecular compound selected from the group consisting of an anionic derivative of cellulose, starch-polyacrylamide, polyvinylpyrrolidone, polymer of maleic acid, and polymer of acrylic acid.

26. An inflatable cuff according to claim 24, wherein said porous sheet is formed of a resin sheet having a multiplicity of fine slits which permit a water coming out from a skin of said body portion of said subject to pass therethrough.

27. An inflatable cuff for pressing a body portion of a living subject by being wound and inflated around the body portion, in measuring a blood pressure of the subject, the cuff comprising:

an inflatable bag which is inflatable by being supplied with air; and a pressing bag including an inner portion which is adapted to contact said body portion of said subject when the cuff is wound around the body portion, and an outer portion which cooperates with said inner portion to provide said pressing bag adapted to press said body portion of said subject, said inflatable bag being accommodated in said pressing bag, a length of each of said inner and outer portions being directly contactable with said inflatable bag said length of said outer portion being formed of a material having an elasticity ensuring that the outer portion is elastically elongateable up to a prescribed maximum amount greater than zero in a circumferential direction of said body portion, when the cuff is inflated around the body portion, said outer portion being elongated because of direct contact with said inflatable bag when the inflatable bag is inflated in said pressing bag.

28. An inflatable cuff for pressing a body portion of a living subject by being wound and inflated around the body portion, in measuring a blood pressure of the subject, the cuff comprising:

an inflatable bag which is inflatable by being supplied with air; and a pressing bag including an inner portion which is adapted to contact said body portion of said subject when the cuff is wound around the body portion, and an outer portion which cooperates with said inner portion to provide said pressing bag adapted to press said body portion of said subject, said inflatable bag being accommodated in said pressing bag, said inner and outer portions being directly contactable with said inflatable bag, said entire outer portion being formed of a material having an elasticity ensuring that the outer portion is elastically elongateable up to a prescribed maximum amount greater than zero in a circumferential direction of said body portion, said outer portion being elongated because of direct contact with said inflatable bag when the inflatable bag is inflated in said pressing bag.

* * * * *